US009040776B2

(12) United States Patent
Martín Trillo et al.

(10) Patent No.: US 9,040,776 B2
(45) Date of Patent: May 26, 2015

(54) GENES REGULATING PLANT BRANCHING, PROMOTORS, GENETIC CONSTRUCTS CONTAINING SAME AND USES THEREOF

(75) Inventors: Mar Martín Trillo, Cantoblanco (ES); María Luisa Rodríguez Buey, Cantoblanco (ES); Pilar Cubas Domínguez, Cantoblanco (ES)

(73) Assignee: Consejo Superior de Investigaciones Cientificas (ES)

( * ) Notice: Subject to any disclaimer, the term of this patent is extended or adjusted under 35 U.S.C. 154(b) by 415 days.

(21) Appl. No.: 13/144,348

(22) PCT Filed: Nov. 27, 2009

(86) PCT No.: PCT/ES2009/070538
§ 371 (c)(1),
(2), (4) Date: Oct. 3, 2011

(87) PCT Pub. No.: WO2010/081917
PCT Pub. Date: Jul. 22, 2010

(65) Prior Publication Data
US 2012/0017337 A1      Jan. 19, 2012

(30) Foreign Application Priority Data
Jan. 13, 2009   (ES) .................................. 200900088

(51) Int. Cl.
| C12N 15/87 | (2006.01) |
| C12N 15/82 | (2006.01) |
| C12N 15/00 | (2006.01) |
| C07H 21/02 | (2006.01) |
| C07H 21/04 | (2006.01) |
| C07K 14/415 | (2006.01) |

(52) U.S. Cl.
CPC .......... C12N 15/8261 (2013.01); C07K 14/415 (2013.01); C12N 15/8218 (2013.01); C12N 15/8226 (2013.01)

(58) Field of Classification Search
USPC ......................................................... 800/290
See application file for complete search history.

(56) References Cited

U.S. PATENT DOCUMENTS

2006/0130178 A1   6/2006   Keetman et al.

FOREIGN PATENT DOCUMENTS

ES        2 249 982        4/2006

OTHER PUBLICATIONS

UniProtKB Accession No. F6KB94 ([online], [retrieved on May 6, 2013], retrieved from the internet <http://www.uniprot.org/uniprot/F6KB94>).*
GenBank Accession No. ER794236 ([online], [retrieved on May 1, 2013], retrieved from the internet < http://www.ncbi.nlm.nih.gov/nucgss/ER794236>).*
GenBank Accession No. DU870963 ([online], [retrieved on May 1, 2013], retrieved from the internet < http://www.ncbi.nlm.nih.gov/nucgss/DU870963>).*
UniProtKB Accession No. F6KB99 ([online], [retrieved on May 6, 2013], retrieved from the internet <http://www.uniprot.org/uniprot/F6KB99>).*
Martin-Trillo et al. (Role of tomato Branched1-like genes in control of shoot branching, 67 Plant J No. 4, 701-714 (2011).*
Lewis et al., Overexpression of the maize Teosinte Branched1 gene in wheat suppresses tiller development, 27 Plant Cell Rep, 1217-1225 at 1217 (2008).*
Aguilar-Martinez et al., Arabidopsis Branched1 acts as an integrator of branching signals with Axillary Buds, 19 Plant Cell, 458-472 (2007).*
Takeda et al., The OsTB1 gene negatively regulates lateral branching in rice, 33 Plant Journal, 513-520 (2003).*
Zhang et al. (A gain-of-function mutation in a plant disease resistance gene leads to constitutive activation of downstream signal transduction pathways in suppressor of npr1-1, constitutive 1, 15 Plant Cell, 2636-2646 at 2639-2641 (2003)).*
Aguilar-Martínez et al., "Arabidopsis Branched1 Acts as an Integrator of Branching Signals within Axillary Buds", The Plant Cell, vol. 19, 2007, pp. 458-472.
Altschul et al., "Basic Local Alignment Search Tool", J. Mol. Biol., vol. 215, 1990, pp. 403-410.
Calipel et al., "Mutation of B-Raf in Human Choroidal Melanoma Cells Mediates Cell Proliferation and Transformation through the MEK/ERK Pathway", The Journal of Biological Chemistry, vol. 278, No. 43, 2003, pp. 42409-42418.
Cubas et al., "The TCP domain: a motif found in proteins regulating plant growth and development", The Plant Journal, vol. 18, No. 2, 1999, pp. 215-222.
Devereux et al., "A comprehensive set of sequence analysis programs for the VAX", Nucleic Acids Research, vol. 12, No. 1, 1984, pp. 387-395.
Doebley et al., "The evolution of apical dominance in maize", Letters to Nature, vol. 386, 1997, pp. 485-488.
Ellul et al., "The ploidy level of transgenic plants in Agrobacterium-mediated transformation of tomato cotyledons (Lycopersicon esculentum L.Mill.) is genotype and procedure dependent", Theor Appl Genet, vol. 106, 2003, pp. 231-238.
Finlayson, "Arabidopsis Teosinte Branched1-Like 1 Regulates Axillary Bud Outgrowth and is Homologous to Monocot Teosinte Branched1", Plant Cell Physiol., vol. 48, No. 5, 2007, pp. 667-677.
Gleave, "A versatile binary vector system with a T-DNA organizational structure conducive to efficient integration of cloned DNA into the plant genome", Plant Molecular Biology, vol. 20, 1992, pp. 1203-1207.
International Search Report for International Application No. PCT/ES2009/070538 mailed Apr. 8, 2010.
Murashige et al. "A Revised Medium for Rapid Growth and Bio Assays with Tobacco Tissue Cultures", Physiologia Plantarum, vol. 15, 1962, pp. 473-497.
Poza-Carrión et al., "Role of TCP Gene Branched1 in the Control of Shoot Branching in Arabidopsis", Plant Signaling & Behavior, vol. 2, Issue 6, 2007, pp. 551-552.
Takeda et al., "The OsTB1 gene negatively regulates lateral branching in rice", The Plant Journal, vol. 33, 2003, pp. 513-520.

* cited by examiner

Primary Examiner — Ashwin Mehta
Assistant Examiner — Rebecca Coobs
(74) Attorney, Agent, or Firm — Merchant & Gould P.C.

(57) ABSTRACT

The invention relates to genes coding for TCP family transcription factors and having a biological role in the development of axillary buds and branch growth. Furthermore, the invention relates to the promoters of the transcription of said genes, to the genetic constructs containing same and to the uses thereof, including the use of agents that modulate the expression of these genes in order to modify plant architecture.

8 Claims, 7 Drawing Sheets

SEQUENCE LISTING

```
<160> NUMBER OF SEQ ID NOS: 52

<210> SEQ ID NO 1
<211> LENGTH: 346
<212> TYPE: PRT
<213> ORGANISM: Solanum lycopersicum

<400> SEQUENCE: 1

Met Tyr Pro Ser Ser Asn Tyr Ser Pro Asn Ile Ser Ser Ser Ser Ser
1               5                   10                  15

Phe Phe His Ile Asn Ile Pro Ser Pro Ser Met Gln Tyr Glu Pro Glu
            20                  25                  30

Phe Ile Gln Tyr Phe His Asp Phe Gln Phe Ile Gln Pro Ser Tyr Asp
        35                  40                  45

Gln Asn Thr Asn Ile Pro Ala Glu Glu Ala Ala Asp Ser Asp Lys Leu
    50                  55                  60

Asp Lys Ile Glu Glu Asp Gln Ser Ile Ile Lys Ser Cys Asn Asn Asn
65                  70                  75                  80

Lys Lys Asp Glu Lys Ser Ser Ser Ser Thr Ser Thr Ile Arg Arg Lys
                85                  90                  95

Asn Asn Lys Arg Thr Thr Ser Gly Ser Ala Gly Val Gly Pro Ser Lys
            100                 105                 110
```

Lys Asp Arg His Ser Lys Ile Asn Thr Ala His Gly Pro Arg Asp Arg
            115                 120                 125

Arg Met Arg Leu Ser Leu Glu Ile Ala Arg Lys Phe Phe Asn Leu Gln
    130                 135                 140

Asp Leu Leu Gly Phe Asp Lys Ala Ser Lys Thr Val Glu Trp Leu Leu
145                 150                 155                 160

Thr Lys Ser Lys Ser Ala Val Asn Asp Leu Val Gln Lys Ile Asn Lys
                165                 170                 175

Asp Lys Cys Ser Gly Ser Glu Asn Pro Asn Ile Ala Thr Val Ser Ser
            180                 185                 190

Pro Ser Ala Glu Ser Cys Glu Val Ile Asp Glu Ser Ala Ala Thr Asn
    195                 200                 205

Thr Ala Glu Thr Gln Lys Gln Gln Lys Lys Val Lys Ser Ile Arg
210                 215                 220

Arg Ala Ile Ile His Pro Val Val Ala Lys Glu Ser Arg Lys Glu Ala
225                 230                 235                 240

Arg Ala Arg Ala Arg Glu Arg Thr Ile Ile Lys Lys Ser Leu Asn Asp
                245                 250                 255

Asn Thr Asn Asn Asn Asn Asn Gly Asp Gln Ser Met Ala Asp Glu Asp
            260                 265                 270

Leu Thr Arg Ser Leu Arg Ser Trp Asn Thr Thr Phe Glu Asp His Gln
    275                 280                 285

Ser Gly Ile Gln Gly Tyr Asn Asn Asn Asn Met Asn Val Val Asp
290                 295                 300

Asn Phe Asn Leu Val Asp Thr Ser Asn Trp Ser Pro Phe Met Phe Asn
305                 310                 315                 320

Tyr His Gln Ile Asn Thr Glu Ile Ser Gln Glu His Gln Phe Ala Asn
                325                 330                 335

Phe Arg Tyr Ser Gly Lys Leu Trp Glu Ala
            340                 345

<210> SEQ ID NO 2
<211> LENGTH: 337
<212> TYPE: PRT
<213> ORGANISM: Solanum lycopersicum

<400> SEQUENCE: 2

Met Gln Tyr Glu His Glu Leu Tyr Phe Gln Ser Phe Asn His Asp Asn
1               5                   10                  15

Gln Tyr Tyr Phe Gln Gln Gln Leu Val Pro Ser Ile Asp Asp Leu
            20                  25                  30

Ser Pro His Ile Leu Ala Asp Ser Cys Thr Glu Ile Ile Thr Lys Pro
        35                  40                  45

Ser Asn Cys Asn His Glu Leu Gln Gly Met Glu Glu Gly Arg Gly Glu
    50                  55                  60

Lys Lys Gly Asp Asp Val Met Ser Ser Arg Ile Ser Gly Arg Ile
65                  70                  75                  80

Ser Lys Asn Asn Lys Arg Ser Ser Asn Lys Asp Arg His Ser Lys Ile
                85                  90                  95

Asn Thr Ala Arg Gly Pro Arg Asp Arg Met Arg Leu Ser Leu Asp
            100                 105                 110

Ala Ala Arg Lys Phe Phe Arg Leu Gln Asp Leu Leu Gly Phe Asp Lys
    115                 120                 125

Ala Ser Lys Thr Val Glu Trp Leu Leu Thr Gln Ser Asp Ser Ala Ile
130                 135                 140

```
Glu Glu Leu Val Ala Ala Lys Gly Asn Asp Ala Gln Val Ala Gln Gln
145                 150                 155                 160

Thr Ser Cys Asn Thr Pro Thr Thr Thr Gly Ile Gly Ala Ile Cys
            165                 170                 175

Ala Ser Asn Ser Ile Ser Glu Ser Cys Glu Val Ile Ser Gly Thr Asp
            180                 185                 190

Glu Thr Ser Ser Asn Asp Lys Asn Lys Glu Thr Ala Gln Asp Glu Glu
            195                 200                 205

Lys Lys Lys Arg Lys Lys Val Val Asn Thr Ala Arg Arg Ala Val Leu
210                 215                 220

Glu Pro Leu Thr Lys Glu Ser Arg Asn Gln Ala Arg Ala Arg Ala Arg
225                 230                 235                 240

Glu Arg Thr Lys Ser Lys Lys Met Ser Gln Thr Gly Lys Ser Lys Ser
            245                 250                 255

Leu Ala Asn Asp Leu Asn Pro Ser Gly Ser Arg Arg Pro Ala Asn Lys
            260                 265                 270

Thr Cys Glu Glu Pro Gly Thr His Glu Glu Leu Asn Phe His Gln Glu
            275                 280                 285

Lys Asn Thr Val Asp Asp Cys Asn Phe Met Val Asn Gly Asn Trp Asn
290                 295                 300

Pro Phe Thr Ile Phe Ser Tyr His Glu Gln Tyr Ala Gly Ile Ser Asn
305                 310                 315                 320

Glu His Gln Leu Val Thr Asp Leu Gln Phe Cys Gly Lys Leu Trp Glu
            325                 330                 335

Gly

<210> SEQ ID NO 3
<211> LENGTH: 353
<212> TYPE: PRT
<213> ORGANISM: Solanum tuberosum

<400> SEQUENCE: 3

Met Tyr Pro Ser Ser Pro Asn Ile Ser Ser Ser Ser Phe Phe His
1               5                   10                  15

Ile Asn Ile Pro Ser Pro Ser Met Gln Tyr Glu Pro Glu Phe Ile Gln
            20                  25                  30

Tyr Phe His Asp Phe Gln Phe Ile Gln Pro Ala Ala Tyr Asp Gln Asn
            35                  40                  45

Asn Leu Asp Thr Asn Ile Thr Ala Glu Glu Ala Asp His Lys Met Glu
            50                  55                  60

Glu Asp Glu Leu Ile Met Lys Ser Cys Lys Asn Lys Lys Asp Glu Ser
65                  70                  75                  80

Thr Ser Thr Thr Thr Thr Ile Arg Arg Lys Asn Asn Lys Arg Thr Thr
            85                  90                  95

Ser Gly Thr Gly Val Gly Pro Ser Lys Lys Asp Arg His Ser Lys Ile
            100                 105                 110

Asn Thr Ala His Gly Pro Arg Asp Arg Arg Met Arg Leu Ser Leu Glu
            115                 120                 125

Ile Ala Arg Lys Phe Phe Asn Leu Gln Asp Leu Leu Gly Phe Asp Lys
            130                 135                 140

Ala Ser Lys Thr Val Glu Trp Leu Leu Thr Lys Ser Lys Ser Ala Val
145                 150                 155                 160

Asn Asp Leu Val Gln Lys Ile Asn Lys Gly Lys Cys Ser Ala Ser Thr
            165                 170                 175
```

```
Asn Pro Asn Ile Gly Val Val Ser Ser Pro Ser Glu Ser Cys Glu Val
            180                 185                 190

Ile Ser Gly Val Ile Asp Glu Ser Ala Ala Thr Asn Asn Thr His Lys
        195                 200                 205

Gln Gln Lys Lys Lys Lys Ser Ile Arg Arg Ala Ile Phe His Pro Val
    210                 215                 220

Val Ala Lys Glu Ser Arg Lys Glu Ala Arg Ala Arg Ala Arg Glu Arg
225                 230                 235                 240

Thr Lys Ile Lys Lys Ser Leu Asn Asn Asn Gly Asp Gln Ser Met
                245                 250                 255

Ala Pro Asp Glu Asp Leu Thr Arg Ser Leu Gly Ser Trp Ser Thr Thr
            260                 265                 270

Phe Glu Asp His Gln Ser Gly Ile Gln Ala Tyr Asn Asn Thr Asn Asn
            275                 280                 285

Ile Met Asn Ala Val Asp Asn Phe Asn Leu Val Asp Thr Ser Asn Trp
        290                 295                 300

Ser Pro Phe Met Phe Asn Tyr His Gln Ile Asn Thr Glu Ile Ser Gln
305                 310                 315                 320

Glu Val Cys Ile Asn Leu Ile Arg Leu Leu Leu Leu Leu Leu Leu Ile
                325                 330                 335

Arg Ser Pro Ile Tyr Leu Phe Leu Phe Leu Phe Phe Cys Cys Ser Ile
            340                 345                 350

Asn

<210> SEQ ID NO 4
<211> LENGTH: 364
<212> TYPE: PRT
<213> ORGANISM: Solanum tuberosum
<220> FEATURE:
<221> NAME/KEY: misc_feature
<222> LOCATION: (28)..(28)
<223> OTHER INFORMATION: Xaa can be any naturally occurring amino acid

<400> SEQUENCE: 4

Met Tyr Pro Pro Ser Asn Asn Asn Cys Asn Tyr Ser Pro Ile Leu Ser
1               5                   10                  15

Ser Phe Ile Cys Gln Asn Ile Pro Ser Ser Pro Xaa Met Gln Tyr Glu
            20                  25                  30

His Glu Leu Tyr Phe Gln Asn Phe Asn His Asp Asp Gln Tyr Tyr Phe
        35                  40                  45

Gln Leu Gln Gln Gln Val Pro Leu Ile Asp Asp Leu Ser Pro His Val
    50                  55                  60

Leu Ala Asp Ser Cys Thr Glu Thr Val Thr Lys Pro Ser Asn Cys Asn
65                  70                  75                  80

His Val Leu Glu Gly Met Glu Glu Gly Arg Gly Gly Asn Lys Gly Asp
                85                  90                  95

Asp Val Val Met Ser Ser Arg Ile Ser Ile Ile Ser Gly Arg Ile Ser
            100                 105                 110

Lys Asn Asn Lys Arg Ser Ser Asn Lys Asp Arg His Ser Lys Ile Asn
        115                 120                 125

Thr Ala Arg Gly Pro Arg Asp Arg Arg Met Arg Leu Ser Leu Asp Ala
    130                 135                 140

Ala Arg Lys Phe Phe Arg Leu Gln Asp Leu Leu Gly Phe Asp Lys Ala
145                 150                 155                 160

Ser Lys Thr Val Glu Trp Leu Leu Thr Gln Ser Asp Ser Ala Ile Glu
                165                 170                 175
```

```
Glu Leu Val Ala Val Lys Gly Asn Asp Ala Gln Val Pro Gln Gln Thr
            180                 185                 190
Ser Cys Asn Thr Pro Thr Thr Thr Gly Ile Gly Ala Ile Cys Ala
            195                 200                 205
Ser Asn Ser Ile Ser Glu Ser Cys Glu Val Ile Ser Gly Thr Asp Glu
        210                 215                 220
Thr Ser Ser Asn Asp Lys Asn Lys Glu Thr Thr Ala Lys Asp Glu Lys
225                 230                 235                 240
Glu Lys Lys Lys Lys Pro Val Asn Thr Ala Arg Arg Pro Ala Phe Glu
                245                 250                 255
Pro Leu Thr Lys Glu Ser Arg Asn Gln Ala Arg Ala Arg Ala Arg Glu
            260                 265                 270
Arg Thr Lys Thr Lys Lys Met Ser Gln Val Gly Lys Ser Lys Ser Pro
            275                 280                 285
Ala His Asp Leu Asn Pro Ser Gly Ser Arg Arg Pro Ala Asn Arg Thr
        290                 295                 300
Cys Glu Glu Pro Gly Thr His Glu Gln His Thr Phe His His Val Asp
305                 310                 315                 320
Asp Ser Ser Phe Val Val Asn Gly Asn Trp Asn Pro Phe Thr Ile Phe
                325                 330                 335
Thr Ser His Glu Gln Tyr Ala Gly Ile Ser Asn Glu His Gln Leu Val
            340                 345                 350
Thr Asp Leu Gln Phe Tyr Gly Lys Leu Trp Glu Ser
            355                 360

<210> SEQ ID NO 5
<211> LENGTH: 1723
<212> TYPE: DNA
<213> ORGANISM: Solanum lycopersicum

<400> SEQUENCE: 5
agtctgaacc cctttcacct caactgtggg aagcaggaag aattcaccaa aactttaata       60
acatattcag taaaaatttt tataatgcgt ctaagaaaag taaaatgtac gtagaattta      120
tcctgcctcg taaaataaaa gattgtatct aaaaaaaacc tcgactcaaa taatacatat      180
taacaaaatt acaaattaac tatcactcaa ccccaatatt tacttcaagt tgttagggat      240
cacttaaggg cctttctttt tctccttttt tttttttttt ttggagaaga tgaaggtgaa      300
agagatggtg gatgatggag ctaggaaaga ggagattgaa gggtattttt tttgtcaaag      360
tatgtgtcag ttgctatcac gtgaacttga aactaagggg caccattaga gaagacttta      420
gctataatat acattcattt ctataaaaaa aaatcacmac ataaacatgc ccttttttaa      480
cttagcttta atatatcttt taaatttgat tatgcagaaa tagatattta aatttatata      540
aaatttaaaa agtctatcta acaatgttgt gtcctacata tattatatct ggtatgatat      600
atatgtgtta cttgtttaat tttatataaa tttaaatatt tatttatgca aattcaaaat      660
taagagatat aaatatcaag ctaaatcgaa gttcaatgaa atatatatat ataattatgc      720
caatataaaa tcagtgtaac tatacaacaa gtactatagt gtcccctcca ctctttttt       780
ctcaaattcc ctttcatact ttaaactccc acatgagcta gctagagaag tctttttttt      840
ttttaaagat tcgkggtgtt tacatcaatt taaacatatt ttgactaatt tcatagaata      900
tttatcatct cttattaata acatgtgtca tattcataaa tgaatagaaa ttactaaata      960
cagtagtact yctttaatt ttttttctaat aaaatttaaa cgtgaaacct catgattcct     1020
aattatccac ttcagtaacc atcgactcac accaacccctt tggtgcaagc gaagccttct    1080
```

```
ttatctttat agcagatagg ggtcctttga aaagatggaa gtacaattac acctctcttt    1140 gtcccttgc aggtaataac ataacatgac ttttctttat cttcatcttt ctttctttgt    1200
caacaagaac ataccaccc atgaatgtct ctcccattag ctaatatatt ccagctaact    1260
agcttaaata tatagtgcta atacytgcac gaacacaaaa atagccacta atatacacct    1320
atacctagct attattatta ttatcataat taagcacwca ccaagcaaca tacatgtaaa    1380
gccacatatt tttaatcacc tgtctttctc aaccaaaaag ctatattatc atcattatat    1440
tgaaaaaaaa attaaaaata accacatatc cttttcccact ttctctatgt gctatctttg    1500
tattcaaaat ttatatatcc aagagaatta tgaagagtct ctctcaaaaa aagttttaat    1560
taatttataa ccttttcttt tttcctactt tttgttgatg cagctaggta gctagattat    1620
taaaagtgtc aaactgaaga agctgatgtt tgtggttatt tcaacttcaa tacaagtgtg    1680
ctaggttgtc cttatcaacc agtttctttt ttttttttta aag                     1723

<210> SEQ ID NO 6
<211> LENGTH: 665
<212> TYPE: DNA
<213> ORGANISM: Solanum lycopersicum

<400> SEQUENCE: 6
tcacatgaag gggcacgata acaagttgtt cgtatccatc cattcacttc caacaatacc      60
gctacgtacc actacctgct tccttcctat ccccagtctt tgtcaaactt cctttccctt     120
tccaattact ttttctttaa tagagatgtt tgtttccttt tccttcccc ccatattctt      180 cccttttttt tttatctctc tttcacaata gtagcaccat gcctgtagct ttgatgctta     240
gacgggcgca cgcgcacgcg cactcacaca actagaatag aatcactctc tctatatatt     300
catagttatc aaaactactt atcatatacc aaaaaaaacc actgtcattc tcaagcaaat     360
aatatttttt ttaaaaaaga agaactacat atatatat agtactacta ctattttcat      420
catcactttg gtcaatccat acagttctaa gtagtcattg cttcctctgt caaattactg     480
tatacagtac attgaactag ctaggggaaa attaatctac taactctaat ttgtttgttt     540
aattctcttc ttattgcagc tagatttgcc taattagcag aaaaaccaaa agctgtgttc     600
atactgtctt tctcaagatc tagacccacc atatagaccg cctcaactac agctactcca     660
caaga                                                                 665

<210> SEQ ID NO 7
<211> LENGTH: 1133
<212> TYPE: DNA
<213> ORGANISM: Solanum lycopersicum

<400> SEQUENCE: 7 atgtacccctt cgagcaatta cagccccaat atttccagct cttcatcttt ctttcacatt      60
aatattccat ctccttctat gcaatatgaa cccgaattca tccaatatt ccatgatttt      120 caattcatcc aacctagtta cgatcagaat accaatattc ctgcagaaga agctgctgat     180
tcggacaaac tagataaaat agaagaagat caatcaatca taaaaagctg caataataac     240
aagaaggatg agaagagtag tagcagtact agtactattc gtagaaaaaa caacaagaga     300
actacgagtg gtagtgctgg tgtaggacct tcgaagaaag atagacacag caaaatcaac     360
acggcacatg gcccaagaga ccgaagaatg agactatcac ttgaaattgc tcgcaaattc     420
ttcaatttgc aagacttgct tgggttcgat aaagccagca aaactgtaga atggctactc     480
acaaagtcaa aatcagcggt gaacgatctg gttcagaaaa ttaacaaaga caaatgcagc     540
```

| | |
|---|---|
| ggtagtgaaa atcctaatat tgctactgta tcatctcctt ccgccgaatc atgtgaagtt | 600 |
| atcgacgaat cagctgcaac taatacagca gaaactcaga agcaacagaa gaaaaaagtt | 660 |
| aagtcgattc gtagggcaat aattcatcca gttgttgcaa aggaatcaag gaaagaagca | 720 |
| agagcaaggg caagggaaag aacaataata aagaaaagcc taaatgataa cacgaataat | 780 |
| aataataatg gtgatcaatc tatggctgat gaggatttaa caagatcatt aagatcttgg | 840 |
| aatactacat ttgaagatca tcaatcaggt attcaaggct ataataataa taataatatg | 900 |
| aatgttgttg ataactttaa tttggtggat actagcaatt ggagcccatt tatgttcaac | 960 |
| tatcaccaaa tcaatactga aatttctcaa gaggtatgta ctaatttaat taataaaatta | 1020 |
| tttttttctat tattattatt aacccgatcg ccaagtattt atttatattt ttgtgttgca | 1080 |
| gcatcaattt gcgaacttcc agtattctgg gaagttatgg gaagcttaat tag | 1133 |

<210> SEQ ID NO 8
<211> LENGTH: 1124
<212> TYPE: DNA
<213> ORGANISM: Solanum lycopersicum

<400> SEQUENCE: 8

| | |
|---|---|
| atgcaatatg aacacgaact atactttcaa agctttaatc atgataacca atattatttt | 60 |
| caacaacagc aactagttcc ctcgatagat gatttgagtc ctcacatctt agctgacagc | 120 |
| tgcaccgaga ttattactaa gccttcgaat tgcaaccacg aactacaagg aatgcaagaa | 180 |
| ggccgaggcg aaaagaaagg agatgatgat gttatgagta gcagaattag tggacggatc | 240 |
| tcaaaaaata ataagagatc ttccaataaa gatcgcacaca gcaagatcaa caccgctcgt | 300 |
| ggtccaagag atcgaaggat gagactttca cttgatgctg ctcgcaagtt tttccgtttg | 360 |
| caggacttat tgggattcga taaggccagc aaaactgttg aatggttgct tactcaatcg | 420 |
| gattctgcaa ttgaagagct tgttgccgct aaaggcaatg atgcacaggt tgctcagcaa | 480 |
| actagctgca atacccccac tactactact ggaattggtg caatttgtgc atctaattct | 540 |
| atttctgagt cgtgtgaagt tatatcagga actgatgaaa cttcctctaa tgacaaaaac | 600 |
| aaggaaaccg ctcaagatga gggagaagaag aaaaggaaga aggtggttaa cacagctcgt | 660 |
| agagctgtgt tagaacctct tacgaaggaa tcgaggaatc aagcaagagc cagggctaga | 720 |
| gagagaacaa aatcaaagaa aatgagccaa actggaaaat ccaaatccct agctaatgat | 780 |
| ttgaacccctt caggatctcg gaggccggct aataaaactt gtgaagaacc tggaacacat | 840 |
| gaagaactca acttccatca agagaagaac actgtcgatg actgtaattt tatggtaaat | 900 |
| ggaaattgga atccatttac aatctttagc tatcatgagc aatacgctgg aatttccaac | 960 |
| gaggtgaggg tttcagactt tgttttttag ggcttcaata attgaaccca catattcttc | 1020 |
| tcatcttctg attattattt ttttaaaaa aaaaaattct tgtttctctg cagcatcaat | 1080 |
| tggttacaga cttgcaattt tgtggaaagc tatgggaagg ctag | 1124 |

<210> SEQ ID NO 9
<211> LENGTH: 1059
<212> TYPE: DNA
<213> ORGANISM: Solanum tuberosum

<400> SEQUENCE: 9

| | |
|---|---|
| atgtacccctt cgagccccaa tatttccagc tcttcatctt tctttcacat taatattcca | 60 |
| tctccttcta tgcaatatga accggaattc atccaatatt ccatgacttt caattcatc | 120 |
| caacctgctg cttacgatca gaataatttg gataccaata ttacggcaga agaagctgat | 180 |

-continued

| | |
|---|---|
| cataagatgg aagaagatga attgatcatg aaaagctgca agaacaagaa ggatgagagt | 240 |
| actagtacca ctactactat tcgtaggaaa acaacaagaa gaactacgag tggtactggt | 300 |
| gtaggacctt cgaagaaaga tagacacagc aaaataaaca cggcacatgg cccaagagac | 360 |
| cgaagaatga gactttcact tgaaattgct agaaaattct tcaatttgca agacttgctt | 420 |
| gggttcgata aggctagcaa aactgtagaa tggctactca caaagtcaaa atcagctgta | 480 |
| aacgatctcg ttcagaaaat taacaaagga aaatgcagcg ctagtacaaa tcctaatatt | 540 |
| ggtgttgtat catctccctc cgagtcatgt gaagtcatat ctggagtaat cgacgaatca | 600 |
| gcagcaacta ataatactca caagcaacag aagaaaaaaa agtcgattcg tagggcaata | 660 |
| tttcatccag ttgttgcaaa ggaatcaagg aaagaagcaa gggcaagggc aagggaaaga | 720 |
| acaaaaataa agaaaagcct aaataataat aatggtgatc aatccatggc gcctgatgag | 780 |
| gatttaacaa gatcattagg atcttggagt actacatttg aagatcatca atcaggtatt | 840 |
| caagcctata ataatactaa caatattatg aatgctgttg ataactttaa tttggtggat | 900 |
| actagcaatt ggagcccatt tatgttcaac tatcaccaaa tcaatactga aatttctcag | 960 |
| gaggtatgta ttaacttaat tagattatta ttattattat tattaatccg atcgccaata | 1020 |
| tatttatttt tatttttatt cttctgttgc agcatcaat | 1059 |

<210> SEQ ID NO 10
<211> LENGTH: 1092
<212> TYPE: DNA
<213> ORGANISM: Solanum tuberosum

<400> SEQUENCE: 10

| | |
|---|---|
| atgtatcctc caagcaacaa taactgcaac tacagcccaa ttttgtcttc tttcatatgc | 60 |
| caaaatattc catcttctcc ttgtatgcaa tatgaacacg aactatactt tcaaaacttc | 120 |
| aatcatgatg accaatatta ttttcaacta cagcaacaag ttcccttgat agatgacttg | 180 |
| agtcctcacg tcttagctga cagctgcact gagactgtta ctaagccttc aaattgcaat | 240 |
| cacgtactag aaggaatgga agaaggccga ggcggaaaca aaggagatga tgttgttatg | 300 |
| agtagcagaa ttagtattat tagtggacgg atctcgaaaa acaataagag atcttccaat | 360 |
| aaggatcgac acagcaagat caacacggct cgtggtccaa gagatcgaag gatgagactt | 420 |
| tcacttgatg ctgctcgcaa gttttttccgt ttgcaggact tgttgggatt tgataaggcc | 480 |
| agcaaaactg tagaatggtt gcttactcaa tcrgattccg caattgaaga gctcgtcgcc | 540 |
| gttaaaggca atgatgctca ggttcctcag caaactagct gcaataccc cactactact | 600 |
| actggaattg gtgcaatttg tgcatctaat tctatttctg agtcatgtga agttatatca | 660 |
| ggaactgatg aaacttcctc taatgacaaa acaaggaaa ctactgctaa agatgagaag | 720 |
| gagaaaaaga agaagccggt taacacagct cgtagacctg cgtttgaacc tcttacaaag | 780 |
| gaatcaagga atcaagcaag agccagggct agagagagaa caaaaacaaa gaaaatgagc | 840 |
| caagttggaa atccaaatc cccagctcat gatttgaacc cttcaggatc tcggaggccg | 900 |
| gctaatagaa cttgtgaaga acctggaaca catgaacaac acaccttcca tcatgttgat | 960 |
| gacagtagtt ttgtggttaa tggaaattgg aatccattta caatcttcac ttctcatgaa | 1020 |
| caatatgctg gaatttccaa tgagcatcaa ttagttacag acttgcaatt ttatggaaag | 1080 |
| ctgtgggaaa gc | 1092 |

<210> SEQ ID NO 11
<211> LENGTH: 225
<212> TYPE: DNA
<213> ORGANISM: Artificial Sequence
<220> FEATURE:
<223> OTHER INFORMATION: iRNA for the gene SlBRC1L1

<400> SEQUENCE: 11

```
tggctactca caaagtcaaa atcagcggtg aacgatctgg ttcagaaaat taacaaagac    60
aaatgcagcg gtagtgaaaa tcctaatatt gctactgtat catctccttc cgccgaatca   120
tgtgaagtta tcgacgaatc agctgcaact aatacagcag aaactcagaa gcaacagaag   180
aaaaaagtta agtcgattcg tagggcaata attcatccag ttgtt                   225
```

<210> SEQ ID NO 12
<211> LENGTH: 415
<212> TYPE: DNA
<213> ORGANISM: Artificial Sequence
<220> FEATURE:
<223> OTHER INFORMATION: iRNA for the gene SlBRC1L2

<400> SEQUENCE: 12

```
caacaccgct cgtggtccaa gagatcgaag gatgagactt tcacttgatg ctgctcgcaa    60 gttttttccgt ttgcaggact tattgggatt cgataaggcc agcaaaactg ttaatggtt   120 gcttactcaa tcggattctg caattgaaga gcttgttgcc gctaaaggca atgatgcaca   180
ggttgctcag caaactagct gcaataccc cactactact actggaattg gtgcaatttg   240
tgcatctaat tctatttctg agtcgtgtga agttatatca ggaactgatg aaacttcctc   300
taatgacaaa acaaggaaa ccgctcaaga tgaggagaag aagaaaagga agaaggtggt   360
taacacagct cgtagagctg tgttagaacc tcttacaaag gaatcgagga atcaa         415
```

<210> SEQ ID NO 13
<211> LENGTH: 185
<212> TYPE: DNA
<213> ORGANISM: Artificial Sequence
<220> FEATURE:
<223> OTHER INFORMATION: iRNA for the gene StBRC1L1

<400> SEQUENCE: 13

```
agaaaattag caaaggaaaa tgcagcgcta gtacaaatcc taatattggt gttgtatcat    60
ctccctccga gtcatgtgaa gtcatatctg gagtaatcga cgaatcagca gcaactaata   120
atactcacaa gcaacagaag aaaaaaaagt cgattcgtag ggcaatattt catccagttg   180
ttgca                                                               185
```

<210> SEQ ID NO 14
<211> LENGTH: 168
<212> TYPE: DNA
<213> ORGANISM: Artificial Sequence
<220> FEATURE:
<223> OTHER INFORMATION: iRNA for the gene StBRC1L2

<400> SEQUENCE: 14

```
gccgttaaag gcaatgatgc tcaggttcct cagcaaacta gctgcaatac ccccactact    60
actactggaa ttggtgcaat ttgtgcatct aattctattt ctgagtcatg tgaagttata   120
tcaggaactg atgaaacttc ctctaatgac aaaaacaagg aaactgct                168
```

```
<210> SEQ ID NO 15
<211> LENGTH: 1041
<212> TYPE: DNA
<213> ORGANISM: Solanum lycopersicum

<400> SEQUENCE: 15 atgtacccttt cgagcaatta cagccccaat atttccagct cttcatcttt ctttcacatt      60
aatattccat ctccttctat gcaatatgaa cccgaattca tccaatattt ccatgatttt     120
caattcatcc aacctagtta cgatcagaat accaatattc ctgcagaaga agctgctgat     180
tcggacaaac tagataaaat agaagaagat caatcaatca taaaaagctg caataataac     240
aagaaggatg agaagagtag tagcagtact agtactattc gtagaaaaaa caacaagaga     300
actacgagtg gtagtgctgg tgtaggacct tcgaagaaag atagacacag caaaatcaac     360
acggcacatg gcccaagaga ccgaagaatg agactatcac ttgaaattgc tcgcaaattc     420
ttcaatttgc aagacttgct tgggttcgat aaagccagca aaactgtaga atggctactc     480
acaaagtcaa atcagcggt gaacgatctg gttcagaaaa ttaacaaaga caatgcagc      540 ggtagtgaaa atcctaatat tgctactgta tcatctcctt ccgccgaatc atgtgaagtt     600
atcgacgaat cagctgcaac taatacagca gaaactcaga agcaacagaa gaaaaaagtt     660
aagtcgattc gtagggcaat aattcatcca gttgttgcaa aggaatcaag gaaagaagca     720
agagcaaggg caagggaaag aacaataata agaaaagcc taaatgataa cacgaataat      780
aataataatg gtgatcaatc tatggctgat gaggatttaa caagatcatt aagatcttgg     840
aatactacat ttgaagatca tcaatcaggt attcaaggct ataataataa taataatatg     900
aatgttgttg ataactttaa tttggtggat actagcaatt ggagcccatt tatgttcaac     960
tatcaccaaa tcaatactga aatttctcaa gagcatcaat ttgcgaactt ccagtattct    1020
gggaagttat gggaagctta a                                              1041

<210> SEQ ID NO 16
<211> LENGTH: 1014
<212> TYPE: DNA
<213> ORGANISM: Solanum lycopersicum

<400> SEQUENCE: 16
atgcaatatg aacacgaact atactttcaa agctttaatc atgataacca atattatttt      60
caacaacagc aactagttcc ctcgatagat gatttgagtc ctcacatctt agctgacagc     120
tgcaccgaga ttattactaa gccttcgaat tgcaaccacg aactacaagg aatggaagaa     180
ggccgaggcg aaaagaaagg agatgatgat gttatgagta gcagaattag tggacggatc     240
tcaaaaaata ataagagatc ttccaataaa gatcgacaca gcaagatcaa caccgctcgt     300
ggtccaagag atcgaaggat gagactttca cttgatgctg ctcgcaagtt tttccgtttg     360
caggacttat tgggattcga taaggccagc aaaactgttg aatggttgct tactcaatcg     420
gattctgcaa ttgaagagct tgttgccgct aaagcaatg atgcacaggt tgctcagcaa      480
actagctgca ataccccac tactactact ggaattggtg caatttgtgc atctaattct      540
atttctgagt cgtgtgaagt tatatcagga actgatgaaa cttcctctaa tgacaaaaac     600
aaggaaaccg ctcaagatga ggagaagaag aaaaggaaga aggtggttaa cacagctcgt     660
agagctgtgt tagaacctct tacgaaggaa tcgaggaatc aagcaagagc cagggctaga     720
gagagaacaa aatcaaagaa aatgagccaa actggaaaat ccaatccct agctaatgat      780 ttgaacccttt caggatctcg gaggccggct aataaaactt gtgaagaacc tggaacacat     840
```

```
gaagaactca acttccatca agagaagaac actgtcgatg actgtaattt tatggtaaat    900
ggaaattgga atccatttac aatctttagc tatcatgagc aatacgctgg aatttccaac    960
gagcatcaat tggttacaga cttgcaattt tgtggaaagc tatgggaagg ctag          1014
```

```
<210> SEQ ID NO 17
<211> LENGTH: 30
<212> TYPE: DNA
<213> ORGANISM: Artificial Sequence
<220> FEATURE:
<223> OTHER INFORMATION: Primer Le1

<400> SEQUENCE: 17 atgtacccttt cgagcaatta cagccccaat                                     30

<210> SEQ ID NO 18
<211> LENGTH: 31
<212> TYPE: DNA
<213> ORGANISM: Artificial Sequence
<220> FEATURE:
<223> OTHER INFORMATION: Primer Le2

<400> SEQUENCE: 18
tatttccagc tcttcatctt tctttcacat t                                    31

<210> SEQ ID NO 19
<211> LENGTH: 22
<212> TYPE: DNA
<213> ORGANISM: Artificial Sequence
<220> FEATURE:
<223> OTHER INFORMATION: Primer LeTCP2-F1

<400> SEQUENCE: 19
caacaccgct cgtggtccaa ga                                              22

<210> SEQ ID NO 20
<211> LENGTH: 28
<212> TYPE: DNA
<213> ORGANISM: Artificial Sequence
<220> FEATURE:
<223> OTHER INFORMATION: Primer LeTCP2-F1 nested

<400> SEQUENCE: 20
ccaagagatc gaaggatgag actttcac                                        28

<210> SEQ ID NO 21
<211> LENGTH: 23
<212> TYPE: DNA
<213> ORGANISM: Artificial Sequence
<220> FEATURE:
<223> OTHER INFORMATION: Primer LeTCP2-R1

<400> SEQUENCE: 21
ttgattcctc gattcctttg taa                                             23

<210> SEQ ID NO 22
<211> LENGTH: 25
<212> TYPE: DNA
<213> ORGANISM: Artificial Sequence
<220> FEATURE:
<223> OTHER INFORMATION: Primer LeTCP2-R1 nested

<400> SEQUENCE: 22
gaggttctaa cacagctcta cgagc                                           25
```

-continued

<210> SEQ ID NO 23
<211> LENGTH: 22
<212> TYPE: DNA
<213> ORGANISM: Artificial Sequence
<220> FEATURE:
<223> OTHER INFORMATION: Primer LeTCP2 cDNA-F

<400> SEQUENCE: 23
gaatgcaata tgaacacgaa ct                                    22

<210> SEQ ID NO 24
<211> LENGTH: 24
<212> TYPE: DNA
<213> ORGANISM: Artificial Sequence
<220> FEATURE:
<223> OTHER INFORMATION: Primer LeTCP2 cDNA-R

<400> SEQUENCE: 24
atgaactgca tcgtagtttt attc                                  24

<210> SEQ ID NO 25
<211> LENGTH: 30
<212> TYPE: DNA
<213> ORGANISM: Artificial Sequence
<220> FEATURE:
<223> OTHER INFORMATION: Primer Le3

<400> SEQUENCE: 25
attgagaatg acttgaaaga taaagatgag                            30

<210> SEQ ID NO 26
<211> LENGTH: 27
<212> TYPE: DNA
<213> ORGANISM: Artificial Sequence
<220> FEATURE:
<223> OTHER INFORMATION: Primer GSP1-TCP1

<400> SEQUENCE: 26
tgtgaaagaa agatgaagag ctggaaa                               27

<210> SEQ ID NO 27
<211> LENGTH: 25
<212> TYPE: DNA
<213> ORGANISM: Artificial Sequence
<220> FEATURE:
<223> OTHER INFORMATION: Primer GSP2-TCP1

<400> SEQUENCE: 27
ttggggctgt aattgctcga agggt                                 25

<210> SEQ ID NO 28
<211> LENGTH: 27
<212> TYPE: DNA
<213> ORGANISM: Artificial Sequence
<220> FEATURE:
<223> OTHER INFORMATION: Primer GSP1-TCP2

<400> SEQUENCE: 28
tcagctaaga tgtgaggact caaatca                               27

<210> SEQ ID NO 29
<211> LENGTH: 28
<212> TYPE: DNA
<213> ORGANISM: Artificial Sequence
<220> FEATURE:
<223> OTHER INFORMATION: Primer GSP2-TCP2

<400> SEQUENCE: 29
atctatcgag ggaactagtt gctgttgt                                          28

<210> SEQ ID NO 30
<211> LENGTH: 34
<212> TYPE: DNA
<213> ORGANISM: Artificial Sequence
<220> FEATURE:
<223> OTHER INFORMATION: Primer for the 5'end of SlBRC1L1

<400> SEQUENCE: 30
ggggctcgag ggatccagaa aattagcaaa ggaa                                    34

<210> SEQ ID NO 31
<211> LENGTH: 34
<212> TYPE: DNA
<213> ORGANISM: Artificial Sequence
<220> FEATURE:
<223> OTHER INFORMATION: Primer for the 5'end of SlBRC1L1

<400> SEQUENCE: 31 gggggggtacc atcgattgca acaactggat gaaa                                   34

<210> SEQ ID NO 32
<211> LENGTH: 40
<212> TYPE: DNA
<213> ORGANISM: Artificial Sequence
<220> FEATURE:
<223> OTHER INFORMATION: Primer for the 5'end of SlBRC1L2

<400> SEQUENCE: 32
ggggctcgag ggatccgccg ttaaaggcaa tgatgctcag                              40

<210> SEQ ID NO 33
<211> LENGTH: 41
<212> TYPE: DNA
<213> ORGANISM: Artificial Sequence
<220> FEATURE:
<223> OTHER INFORMATION: Primer for the 5'end of SlBRC1L2

<400> SEQUENCE: 33 gggggggtacc atcgatagca gtttccttgt ttttgtcatt a                           41

<210> SEQ ID NO 34
<211> LENGTH: 26
<212> TYPE: DNA
<213> ORGANISM: Artificial Sequence
<220> FEATURE:
<223> OTHER INFORMATION: Primer racest1-5'

<400> SEQUENCE: 34
tgggctccaa ttgctagtat ccacca                                             26

<210> SEQ ID NO 35
<211> LENGTH: 26
<212> TYPE: DNA
<213> ORGANISM: Artificial Sequence
<220> FEATURE:
<223> OTHER INFORMATION: Primer StTCP1-ORF1

<400> SEQUENCE: 35 atgtacccctt cgagccccaa tatttc                                            26

```
<210> SEQ ID NO 36
<211> LENGTH: 34
<212> TYPE: DNA
<213> ORGANISM: Artificial Sequence
<220> FEATURE:
<223> OTHER INFORMATION: Primer B26

<400> SEQUENCE: 36
gactcgagtc gacatcgttt ttttttttt tttt                                34

<210> SEQ ID NO 37
<211> LENGTH: 17
<212> TYPE: DNA
<213> ORGANISM: Artificial Sequence
<220> FEATURE:
<223> OTHER INFORMATION: Primer B25

<400> SEQUENCE: 37
gactcgagtc gacatcg                                                  17

<210> SEQ ID NO 38
<211> LENGTH: 27
<212> TYPE: DNA
<213> ORGANISM: Artificial Sequence
<220> FEATURE:
<223> OTHER INFORMATION: Primer genomic-StTCP1A

<400> SEQUENCE: 38
tgaatagaag tgtagtaggt tgtcctt                                       27

<210> SEQ ID NO 39
<211> LENGTH: 25
<212> TYPE: DNA
<213> ORGANISM: Artificial Sequence
<220> FEATURE:
<223> OTHER INFORMATION: Primer genomic-StTCP1B

<400> SEQUENCE: 39
tgaaagataa agatgagctt attta                                         25

<210> SEQ ID NO 40
<211> LENGTH: 29
<212> TYPE: DNA
<213> ORGANISM: Artificial Sequence
<220> FEATURE:
<223> OTHER INFORMATION: Primer StTCP2-A

<400> SEQUENCE: 40
agagatcttc caataaggat cgacacagc                                     29

<210> SEQ ID NO 41
<211> LENGTH: 29
<212> TYPE: DNA
<213> ORGANISM: Artificial Sequence
<220> FEATURE:
<223> OTHER INFORMATION: Primer StTCP2-B

<400> SEQUENCE: 41
atcaacacgg tcgtgggtcc aagagatcg                                     29

<210> SEQ ID NO 42
<211> LENGTH: 30
<212> TYPE: DNA
<213> ORGANISM: Artificial Sequence
<220> FEATURE:
<223> OTHER INFORMATION: Primer St2-Seq 1
```

<400> SEQUENCE: 42
tcatctcctt tgtttccgcc tcggccttct                30

<210> SEQ ID NO 43
<211> LENGTH: 27
<212> TYPE: DNA
<213> ORGANISM: Artificial Sequence
<220> FEATURE:
<223> OTHER INFORMATION: Pimer St2-Seq 2

<400> SEQUENCE: 43
cttccattcc ttctagtacg tgattgc                27

<210> SEQ ID NO 44
<211> LENGTH: 26
<212> TYPE: DNA
<213> ORGANISM: Artificial Sequence
<220> FEATURE:
<223> OTHER INFORMATION: Primer StTCP2-5'

<400> SEQUENCE: 44
atgtatcctc caagcaacaa taactg                26

<210> SEQ ID NO 45
<211> LENGTH: 28
<212> TYPE: DNA
<213> ORGANISM: Artificial Sequence
<220> FEATURE:
<223> OTHER INFORMATION: Primer StTCP2-3'

<400> SEQUENCE: 45
gctttcccac agctttccat aaaattgc                28

<210> SEQ ID NO 46
<211> LENGTH: 34
<212> TYPE: DNA
<213> ORGANISM: Artificial Sequence
<220> FEATURE:
<223> OTHER INFORMATION: Primer of the 5'end of StBRC1L1

<400> SEQUENCE: 46
ggggctcgag ggatccagaa aattagcaaa ggaa                34

<210> SEQ ID NO 47
<211> LENGTH: 34
<212> TYPE: DNA
<213> ORGANISM: Artificial Sequence
<220> FEATURE:
<223> OTHER INFORMATION: Primer of the 3'end of StBRC1L1

<400> SEQUENCE: 47 gggggggtacc atcgattgca acaactggat gaaa                34

<210> SEQ ID NO 48
<211> LENGTH: 40
<212> TYPE: DNA
<213> ORGANISM: Artificial Sequence
<220> FEATURE:
<223> OTHER INFORMATION: Primer of the 5'end

<400> SEQUENCE: 48
ggggctcgag ggatccgccg ttaaaggcaa tgatgctcag                40

<210> SEQ ID NO 49
<211> LENGTH: 41
<212> TYPE: DNA
<213> ORGANISM: Artificial Sequence
<220> FEATURE:
<223> OTHER INFORMATION: Primer of the 3'end of the gene StBRC1L2

<400> SEQUENCE: 49 gggggggtacc atcgatagca gtttccttgt ttttgtcatt a                         41

<210> SEQ ID NO 50
<211> LENGTH: 325
<212> TYPE: PRT
<213> ORGANISM: Solanum lycopersicum

<400> SEQUENCE: 50

Met Tyr Pro Ser Ser Asn Tyr Ser Pro Asn Ile Ser Ser Ser Ser Ser
1               5                   10                  15

Phe Phe His Ile Asn Ile Pro Ser Pro Ser Met Gln Tyr Glu Pro Glu
            20                  25                  30

Phe Ile Gln Tyr Phe His Asp Phe Gln Phe Ile Gln Pro Ser Tyr Asp
        35                  40                  45

Gln Asn Thr Asn Ile Pro Ala Glu Glu Ala Ala Asp Ser Asp Lys Leu
    50                  55                  60

Asp Lys Ile Glu Glu Asp Gln Ser Ile Ile Lys Ser Cys Asn Asn Asn
65                  70                  75                  80

Lys Lys Asp Glu Lys Ser Ser Ser Thr Ser Thr Ile Arg Arg Lys
                85                  90                  95

Asn Asn Lys Arg Thr Thr Ser Gly Ser Ala Gly Val Gly Pro Ser Lys
            100                 105                 110

Lys Asp Arg His Ser Lys Ile Asn Thr Ala His Gly Pro Arg Asp Arg
        115                 120                 125

Arg Met Arg Leu Ser Leu Glu Ile Ala Arg Lys Phe Phe Asn Leu Gln
    130                 135                 140

Asp Leu Leu Gly Phe Asp Lys Ala Ser Lys Thr Val Glu Trp Leu Leu
145                 150                 155                 160

Thr Lys Ser Lys Ser Ala Val Asn Asp Leu Val Gln Lys Ile Asn Lys
                165                 170                 175

Asp Lys Cys Ser Gly Ser Glu Asn Pro Asn Ile Ala Thr Val Ser Ser
            180                 185                 190

Pro Ser Ala Glu Ser Cys Glu Val Ile Asp Glu Ser Ala Ala Thr Asn
        195                 200                 205

Thr Ala Glu Thr Gln Lys Gln Gln Lys Lys Val Lys Ser Ile Arg
    210                 215                 220

Arg Ala Ile Ile His Pro Val Val Ala Lys Ser Arg Lys Glu Ala
225                 230                 235                 240

Arg Ala Arg Ala Arg Glu Arg Thr Ile Ile Lys Lys Ser Leu Asn Asp
                245                 250                 255

Asn Thr Asn Asn Asn Asn Gly Asp Gln Ser Met Ala Asp Glu Asp
            260                 265                 270

Leu Thr Arg Ser Leu Arg Ser Trp Asn Thr Thr Phe Glu Asp His Gln
        275                 280                 285

Ser Ala Ile Gly Ala His Leu Cys Ser Thr Ile Thr Lys Ser Ile Leu
    290                 295                 300

```
Lys Phe Leu Lys Ser Ile Asn Leu Arg Thr Ser Ser Ile Leu Gly Ser
305                 310                 315                 320

Tyr Gly Lys Leu Asn
            325

<210> SEQ ID NO 51
<211> LENGTH: 362
<212> TYPE: PRT
<213> ORGANISM: Solanum tuberosum
<220> FEATURE:
<221> NAME/KEY: misc_feature
<222> LOCATION: (28)..(28)
<223> OTHER INFORMATION: Xaa can be any naturally occurring amino acid

<400> SEQUENCE: 51

Met Tyr Pro Pro Ser Asn Asn Cys Asn Tyr Ser Pro Ile Leu Ser
1               5                   10                  15

Ser Phe Ile Cys Gln Asn Ile Pro Ser Ser Pro Xaa Met Gln Tyr Glu
                20                  25                  30

His Glu Leu Tyr Phe Gln Asn Phe Asn His Asp Asp Gln Tyr Tyr Phe
            35                  40                  45

Gln Leu Gln Gln Gln Val Pro Leu Ile Asp Asp Leu Ser Pro His Val
50                  55                  60

Leu Ala Asp Ser Cys Thr Glu Thr Val Thr Lys Pro Ser Asn Cys Asn
65                  70                  75                  80

His Val Leu Glu Gly Met Glu Glu Gly Arg Gly Gly Asn Lys Gly Asp
                85                  90                  95

Asp Val Met Ser Ser Arg Ile Ser Ile Ile Ser Gly Arg Ile Ser Lys
            100                 105                 110

Asn Asn Lys Arg Ser Ser Asn Lys Asp Arg His Ser Lys Ile Asn Thr
        115                 120                 125

Ala Arg Gly Pro Arg Asp Arg Arg Met Arg Leu Ser Leu Asp Ala Ala
130                 135                 140

Arg Lys Phe Phe Arg Leu Gln Asp Leu Leu Gly Phe Asp Lys Ala Ser
145                 150                 155                 160

Lys Thr Val Glu Trp Leu Leu Thr Gln Ser Asp Ser Ala Ile Glu Glu
                165                 170                 175

Leu Val Ala Val Lys Gly Asn Asp Ala Gln Val Pro Gln Gln Thr Ser
            180                 185                 190

Cys Asn Thr Pro Thr Thr Thr Gly Ile Gly Ala Ile Cys Ala Ser
        195                 200                 205

Asn Ser Ile Ser Glu Ser Cys Glu Val Ile Ser Gly Thr Asp Glu Thr
210                 215                 220

Ser Ser Asn Asp Lys Asn Lys Glu Thr Ala Lys Asp Glu Lys Glu Lys
225                 230                 235                 240

Lys Lys Lys Pro Val Asn Thr Ala Arg Ala Ala Phe Glu Pro Leu
                245                 250                 255

Thr Lys Glu Ser Arg Asn Gln Ala Arg Ala Arg Ala Arg Glu Arg Thr
            260                 265                 270

Lys Thr Lys Lys Met Ser Gln Val Gly Lys Ser Lys Pro Val His
        275                 280                 285

Asp Leu Asn Pro Ser Gly Ser Arg Arg Pro Ala Asn Arg Thr Cys Glu
290                 295                 300

Glu Pro Gly Thr His Glu Gln His Thr Phe His His Val Asp Asp Thr
305                 310                 315                 320
```

```
Asn Phe Val Val Asn Gly Asn Trp Asn Pro Phe Thr Ile Phe Ser Ser
                325                 330                 335

His Glu Gln Tyr Ala Gly Ile Ser Asn Glu His Gln Leu Val Thr Asp
            340                 345                 350

Leu Gln Phe Tyr Gly Lys Leu Trp Glu Ser
        355                 360

<210> SEQ ID NO 52
<211> LENGTH: 1086
<212> TYPE: DNA
<213> ORGANISM: Solanum tuberosum

<400> SEQUENCE: 52
atgtatcctc caagcaacaa taactgcaac tacagcccaa ttttgtcttc tttcatatgc       60
caaaatattc catcttctcc ttgtatgcaa tatgaacacg aactatactt tcaaaacttc      120
aatcatgatg accaatatta ttttcaacta cagcaacaag ttcccttgat agatgacttg      180
agtcctcacg tcttagctga cagctgcact gagactgtta ctaagccttc aaattgcaat      240
cacgtactag aaggaatgga agaaggccga ggcggaaaca aaggagatga tgttatgagt      300
agcagaatta gtattattag tggacggatc tcaaaaaaca ataagagatc ttccaataag      360
gatcgacaca gcaagatcaa cacggctcgt ggtccaagag atcgaaggat gagactttca      420
cttgatgctg ctcgcaagtt tttccgtttg caggacttat tgggatttga taaggccagc      480
aaaactgtag aatggttgct tactcaatca gattccgcaa ttgaagagct cgtcgccgtt      540
aaaggcaatg atgctcaggt tcctcagcaa actagctgca ataccccac tactactact       600 ggaattggtg caatttgtgc atctaattct atttctgagt catgtgaagt tatatcagga      660
actgatgaaa cttcctctaa tgacaaaaac aaggaaactg ctaaagatga gaaggagaaa      720
aagaagaagc cggttaacac agctcgtaga gctgcgtttg aacctcttac aaaggaatca      780
aggaatcaag caagagccag ggctagagag agaacaaaaa caaagaaaat gagccaagtt      840
ggaaaatcca aatccccagc tcatgatttg aacccttcag gatctcggag gccggctaat      900
agaacttgtg aagaacctgg aacacatgaa caacacacct tccatcatgt tgatgacact      960
aattttgtgg ttaatggaaa ttggaatcca tttacaatct tcagctctca tgaacaatat     1020
gctggaattt ccaatgagca tcaattagtt acagacttgc aattttatgg aaagctgtgg     1080
gaaagc                                                                1086
```

GENES REGULATING PLANT BRANCHING, PROMOTORS, GENETIC CONSTRUCTS CONTAINING SAME AND USES THEREOF

This application is a National Stage Application of PCT/ES2009/070538, filed 27 Nov. 2009, which claims benefit of Serial. No. P200900088, filed 13 Jan. 2009 in Spain and which applications are incorporated herein by reference. To the extent appropriate, a claim of priority is made to each of the above disclosed applications.

The present invention belongs to the field of molecular biology, biotechnology and plant improvement, and specifically relates to genes coding for transcription factors of the TCP family and having a biological role in the development of the axillary buds and branch growth. It also relates to the transcription promoters of said genes, to the genetic constructs containing same and to the uses thereof, including the use of agents that modulate the expression of these genes, to modify the plant architecture.

PRIOR ART

One of the central questions in biology is the effect of the evolution of genomes in morphological diversity. The body plans are determined by the genetic routes of development widely conserved in large taxonomic groups. Changes in the activity of the genes that control these pathways give rise to alterations in the morphological templates. Most of these changes are deleterious, but a few may give rise to evolution in the form.

In angiosperm plants the branching templates are determined by the position in which the branches are formed. The branches are generated from meristems formed in the axillary buds of the leaves after germination of the seeds. The axillary meristems (AM) give rise to axillary buds, structures containing preformed branches with short internodes, leaf primordia, new AM and, often, floral meristems. The buds can remain inactive during long periods of time or sprout giving rise to branches due to elongation of the internodes, in response to environmental or endogenous signals. This decision determines the plant architecture and affects key aspects of plant life, such as the amount of nutrients each growth axis will receive, plant height, the sun protection of the fruit, efficiency in light absorption or their visibility for pollenizers.

The genes that control the start of the AM, the development of the buds and their sprouting have been characterized in different species of angiosperms. These studies indicate that the development of the axillary buds is controlled by conserved genetic routes which evolved before the radiation of the plants with flowers. The start of AM is controlled by the genes Ls/LAS/MONOCULM1 and the genes Blind/RAX1 in tomatoes (*Solanum lycopersicum*), *Arabidopsis*, and rice. Auxin and strigolactone, hormones synthesized in the apices of the shoots and in the root, respectively, promote long-distance signalling to suppress branching in various species. The synthesis and the response to the strigolactones through the conserved pathway MAX/RMS, described in *Arabidopsis* and pea, have also been found in petunia monocotyledon (*Petunia hybrida*), and rice. The genes which act within the buds delaying their development and growth are also conserved. The gene Teosinte branched1 (Tb1) isolated in corn and in other monocotyledon codes for a transcription factor of the TCP family. The TCP genes, exclusive of plants, code for transcription factors containing the so-called TCP domain, a sequence of 59 amino acids with a basic region and a helix-loop-helix domain, which gives DNA linking capacity and to other proteins (Cubas et al., 1999. *Plant Journal*. 18:215-222), which is expressed in the AM and in the axillary buds, where its growth is suppressed. Tb1 also controls the flowering and the development of inflorescence. In dicotyledon, the duplication of Tb1 has given rise to three types of genes (CYC1, CYC2 and CYC3) one of which, CYC1-type, seems to have retains the majority of the branching suppression activity, at least in *Arabidopsis*, where this gene receives the name of BRANCHED1 (BRC1). BRC1 acts within the buds preventing their development. BRC1 is controlled transcriptionally by the MAX route and responds to environmental and developmental stimuli suppressing the branching.

Despite the fact that the genes having a key role in the control of axillary development are very conserved, the diversity of the branching models found in angiosperms suggest that the modulation of this process has diverged into different phylogenetic groups (clades), which is supported by the different regulation of the genes of MAX type in pea, *Arabidopsis* and rice. It is very possible that the function and regulation evolution of the BRC1 type genes have also played an important role in this evolution. Unlike the alterations in the signalling pathways, which often generate undesired pleiotropic effects, the modifications in the regulation of transcription factors which are locally expressed, such as BRC1, which exclusively acts in the axillary buds, could be more easily tolerated. The transcriptional regulations have played a key role in the evolution of many morphological features. Indeed, during the domestication of corn, the genetic improvement for obtaining plants with a strong apical dominance, gave rise to the selection of plants that overexpress Tb1. CYCLOIDEA, another transcription factor of the TCP family, has been responsible for the evolution of floral bilateral symmetry, a morphological innovation which has evolved independently in different clades.

The control of the development of the axillary buds has a great applied potential since knowing its genetic bases allows us to control the architecture of plants of agronomic interest.

By inhibition of the axillary development we can promote the growth in a single axis favouring long stems and with few nodes as is desirable, for example, in species of ligneous plants which are used for wood production, others that are grown at high density such as gramineae or those wherein the side stems are an obstacle for mechanized collection. We can favour the contribution of nutrients to the axes which are developing fruits (e.g. tomato) or extending the storage life of certain products whose shoots reduce their quality (e.g. potatoes, onions, garlic). The classic improvement has made it possible to obtain varieties with a single stem or "monostem" in some species (e.g. sunflower); however, in others (e.g. tobacco, tomato) it has not been possible to achieve having this character in high production lines. The alternative techniques used for obtaining plants with a single stem (manual elimination of side branches, application of chemical products) not only make the production more expensive, but they favour the propagation of diseases and may entail problems of environmental pollution. Favouring axillary development, we can generate shrubby architectures and increase the production of leaves and flowers, elements appreciated in ornamental species or in those where the fruit are the products of consumption. The increase in the formation of shoots also has interest in species which are used for the carpeting of land, wherein compact growth is valued (e.g. gramineae for lawns or pastures). It would be of great ecological value to promote the intercalated growth in creeper species adapted to arid lands threatened by erosion wherein grass is costly to maintain. The production of new shoots also has importance in plant propagation and in vitro culture.

Finally, in certain ligneous species, the control of sprouting of the axillary buds whose physiological and hormonal regulation is comparable with that of herbaceous plants has great economic importance. In vines, cherry trees, apple trees and ligneous species, the axillary buds require an exposure to the cold during days or weeks to sprout. These species have been begun to be grown in warm countries (e.g. Brazil and Thailand) wherein low temperatures are not usually reached, for which reason the farmers are obliged to use, to make the buds sprout, very toxic chemical treatments (hydrocyanic acid, dinitro-orthocresol), or costly hormonal treatments which are quickly degraded and produce undesired effects.

The Solanaceae, and among them the tomato plant (*Solanum lycopersicum*) and the potato plant (*Solanum tuberosum*), are plants of great economic importance, where some of their agricultural characteristics of interest depend on the activity of their axillary buds. The sprouting of the buds alters the relation between the production and consumption of photoassimilates, and can affect production.

Therefore in fields such as agriculture, forestry and horticulture, it would be of great interest to be able to control the development of the axillary buds and the elongation of branches.

DESCRIPTION OF THE INVENTION

The authors of the present invention have isolated and researched the role of the orthologous genes of Teosinte branched1 of corn and BRANCHED1 (BRC1) of *Arabidopsis* in two species of the Solanaceae family, the tomato plant (*Solanum lycopersicum* L.) and the potato plant (*Solanum tuberosum* L.). These genes code for transcription factors of the TCP family. The TCP proteins, exclusive of plants, are transcription factors with a BHLH domain which gives DNA linking capacity and to other proteins. In *Arabidopsis* the role of BRC1 has been demonstrated as repressor during the initiation of the axillary meristems, the development of the buds and branch growth.

The authors have found that there are two genes related to BRC1 in each species (called SlBRC1L1 and SlBRC1L2, in the tomato plant and StBRC1L1 and StBRC1L2 in the potato plant). They have also demonstrated that, in both species, BRC1L1 and BRC1L2 play a fundamental role in suppressing the development of axillary buds and branch elongation. In the potato, StBRC1L1 and StBRC1L2 also control the formation of the stolons and their branching, and the sprouting of the tuber eyes. BRC1L1 and BRC1L2 are specifically expressed in axillary buds but their expression levels are different for each gene. The function loss phenotype of each one indicates that, although both control the branching, each gene has a certain degree of specialization and functional divergence: in the potato, StBRC1L1 would preferably control the branching of the stolons and StBRC1L2 the elongation of aerial branches; in the tomato plant, SlBRC1L2 could play a more important role than SlBRC1L1 in the control of the branch elongation.

Therefore, the sequences of nucleic acids that code for the proteins product of these genes, promoters and the genetic constructions product of this invention constitute a valuable tool for manipulation of the development of the axillary buds, and the branching control, to increase plant yield, and in particular of the potato and the tomato. The invention also relates to the genetic constructions comprising these sequences, as well as transformed cells, vectors and transgenic plants which incorporate them. It also relates to agents modulating expression, and therefore, biological activity, of these genes, as well as new compositions including these modulating agents, and the use of these sequences, genetic constructions, modulating agents and compositions for the manipulation of the axillary buds, the growth and the branching of the plants, and, in particular, of the tomato plant and of potato.

The present invention also comprises methods for manipulating the plant architecture, in particular the branching, and therefore the yield of said plants incorporating the expression and/or inhibition constructions of the invention.

In the particular case of these two species of Solanaceae, the inhibition of the expression of the new genes (SlBRC1L1, SlBRC1L2, StBRC1L1, StBRC1L2) by RNA interfering technology (RNAi), increases aerial branching in the case of the tomato plant (only the inhibition of SlBRC1L2) and, in the case of the potato plant further increases the production of stolons and their branching, increasing the agricultural yield of this species. Increasing the expression of these new genes, in contrast, would give rise to a reduction in the number of branches, in the case of the tomato plant, favouring the contribution of nutrients to the axes which are developing fruit, and avoiding the use of alternative techniques used for obtaining plants with a single stem (such as the manual pruning of the side branches or the application of chemical products) which not only make production more expensive, but also favour the propagation of disease and may entail problems of environmental contamination.

Therefore, a first aspect of this invention relates to an isolated RNA or DNA polynucleotide, hereinafter first polynucleotide of the invention, capable of being translated into an amino acid sequence comprising a peptide having an identity with SEQ ID NO: 1, selected from any of the following:
   a) at least 95%, or
   b) at least 99%.

In a preferred embodiment of this aspect of the invention, the isolated RNA or DNA polynucleotide is capable of being translated into amino acid sequence SEQ ID NO: 1.

Another aspect of this invention relates to an isolated RNA or DNA polynucleotide, hereinafter second polynucleotide of the invention, capable of being translated into an amino acid sequence comprising a peptide having an identity with SEQ ID NO: 2 selected from any of the following:
   a) at least 95%, or
   b) at least 99%.

In a preferred embodiment of this aspect of the invention, the isolated RNA or DNA polynucleotide is capable of being translated into amino acid sequence SEQ ID NO: 2.

Another aspect of this invention relates to an isolated RNA or DNA polynucleotide, hereinafter third polynucleotide of the invention, capable of being translated into an amino acid sequence comprising a peptide having an identity with SEQ ID NO: 3 selected from any of the following:
   a) at least 95%, or
   b) at least 99%.

In a preferred embodiment of this aspect of the invention, the isolated RNA or DNA polynucleotide is capable of being translated into amino acid sequence SEQ ID NO: 3.

Another aspect of this invention relates to an isolated RNA or DNA polynucleotide, hereinafter fourth polynucleotide of the invention, capable of being translated into an amino acid sequence comprising a peptide having an identity with SEQ ID NO: 4 selected from any of the following:
   a) at least 95%, or
   b) at least 99%.

In a preferred embodiment of this aspect of the invention, the isolated RNA or DNA polynucleotide is capable of being translated into amino acid sequence SEQ ID NO: 4.

The gene SlBRC1L1 is translated into two proteins, a long one, of 346 amino acids (SEQ ID NO: 1) and another short one, of 325 amino acids (SEQ ID NO: 50). Therefore, another aspect of this invention relates to an isolated RNA or DNA polynucleotide, hereinafter eleventh polynucleotide of the invention, capable of being translated into an amino acid sequence comprising a peptide having an identity with SEQ ID NO: 50 selected from any of the following:
 a) at least 95%, or
 b) at least 99%.

In a preferred embodiment of this aspect of the invention, the isolated RNA or DNA polynucleotide is capable of being translated into amino acid sequence SEQ ID NO: 50.

The authors of the present invention have also detected the regulatory expression sequences of said genes, which are capable of directing the expression of a gene of interest in axillary meristems but not in apical meristems in the tomato. The use of a promoter such as that provided by this invention makes it possible to genetically manipulate the plants and obtain plants with improved characteristics, making it possible to modify the plant architecture altering the growth or development of its axillary buds without altering the growth of the main axis.

Therefore, another aspect of this invention relates to an isolated RNA or DNA polynucleotide, hereinafter fifth polynucleotide of the invention, capable of directing the expression of a gene of interest in the axillary buds, having an identity with SEQ ID NO: 5 selected from any of the following:
 a) at least 95%, or
 b) at least 99%.

In a preferred embodiment of this aspect of the invention, the isolated RNA or DNA polynucleotide has the nucleotide sequence included in SEQ ID NO: 5.

Another aspect of this invention relates to an isolated RNA or DNA polynucleotide, hereinafter sixth polynucleotide of the invention, capable of directing the expression of a gene of interest in the axillary buds, having an identity with SEQ ID NO: 6 selected from any of the following:
 a) at least 95%, or
 b) at least 99%.

In a preferred embodiment of this aspect of the invention, the isolated RNA or DNA polynucleotide has the nucleotide sequence included in SEQ ID NO: 6.

It can be expected that the degree of identity/similarity of the proteins homologous to those included in sequences SEQ ID NO: 1 and SEQ ID NO: 2 (for the tomato plant), and SEQ ID NO: 3, SEQ ID NO: 4 (for the potato), are, in different varieties and subspecies of *Solanum lycopersicum* L. and *Solanum tuberosum* L., of at least 80% or greater, and more preferably of at least 85%, 90, 95% or 99%. The correspondence between the amino acid sequence(s) of the putative sequence(s) and the sequences included in SEQ ID NO: 1, SEQ ID NO: 2, SEQ ID NO: 3 and SEQ ID NO: 4 can be determined by methods known in the state of the art. The methods for sequence comparison are known in the state of the art, and include, although without being limited to them, the program BLASTP or BLASTN, and FASTA (Altschul et al., *J. Mol. Biol.* 215: 403-410 (1999).

The term "homology", as used in this specification, refers to the similarity between two structures due to a common evolutionary ancestry, and more specifically, to the similarity between two or more sequences of nucleotides or amino acids. Since two sequences are considered homologous if they have the same evolutionary origin, in general, it is assumed that values of similarity or identity higher than 95% would indicate homology. We can consider, therefore, that percentages of identity of, at least, 99%, could maintain the function of the orthologous amino acid sequences included in SEQ ID NO: 1, SEQ ID NO: 2, SEQ ID NO: 3 and SEQ ID NO: 4.

The term "orthologous" refers to homologous structures of different species, having a common ancestor, and in particular, to the similarity between two or more sequences of nucleotides or amino acids.

The term "identity", as used in this specification, refers to the proportion of identical nucleotides or amino acids between two nucleotide or amino acid sequences compared. The methods of comparison of sequences are known in the state of the art, and include, but are not limited to, the GAG program, including GAP (Devereux et al., *Nucleic Acids Research* 12: 287 (1984) Genetics Computer Group University of Wisconsin, Madison, (WI); BLAST, BLASTP or BLASTN, and FASTA (Altschul et al., *J. Mol. Biol.* 215: 403-410 (1999).

In another aspect of the invention a genetic construction of DNA or RNA is provided, hereinafter first genetic construction of the invention, comprising one of the following types of sequences:
 a) sequence of nucleotides, comprising, at least, the first polynucleotide of the invention, or the coding sequence of SEQ ID NO: 1, for its transcription in vitro or in vivo, or
 b) sequence of nucleotides, corresponding to a gene expression system or vector comprising the first polynucleotide of the invention, operatively linked to, at least, one promoter which directs the transcription of said sequence of nucleotides, and to other sequences necessary or appropriate for the transcription and their suitable regulation in time and place, for example, initiation and termination signals, cleavage sites, polyadenylation signals, replication origin, transcriptional enhancers, transcriptional silencers, etc.

In a preferred embodiment of this aspect of the invention, the promoter is the fifth polynucleotide of the invention.

In another aspect of the invention a genetic construction of DNA or RNA is provided hereinafter second genetic construction of the invention, comprising one of the following types of sequences:
 a) sequence of nucleotides, comprising, at least, the second polynucleotide of the invention, or the coding sequence of SEQ ID NO: 2, for its transcription in vitro or in vivo, or
 b) sequence of nucleotides, corresponding to a gene expression system or vector comprising the second polynucleotide of the invention, operatively linked to, at least, one promoter which directs the transcription of said sequence of nucleotides, and to other sequences necessary or appropriate for the transcription and their suitable regulation in time and place, for example, initiation and termination signals, cleavage sites, polyadenylation signals, replication origin, transcriptional enhancers, transcriptional silencers, etc.

In a preferred embodiment of this aspect of the invention, the promoter is the sixth polynucleotide of the invention.

In another aspect of the invention a genetic construction of DNA or RNA is provided, hereinafter third genetic construction of the invention, comprising one of the following types of sequences:
 a) sequence of nucleotides, comprising, at least, the third polynucleotide of the invention, or the coding sequence of SEQ ID NO: 3, for its transcription in vitro or in vivo, or
 b) sequence of nucleotides, corresponding to a gene expression system or vector comprising the third polynucleotide of the invention, operatively linked to, at least, one promoter which directs the transcription of said sequence of nucleotides, and to other sequences necessary or appropriate for the transcription and their suitable regulation in time and place, for example, initiation and termination signals, cleavage sites, polyadenylation signals, replication origin, transcriptional enhancers, transcriptional silencers, etc.

In another aspect of the invention a genetic construction of DNA or RNA is provided, hereinafter fourth genetic construction of the invention, comprising one of the following types of sequences:

a) sequence of nucleotides, comprising, at least, the fourth polynucleotide of the invention, or the coding sequence of SEQ ID NO: 4, for its transcription in vitro or in vivo, or b) sequence of nucleotides, corresponding to a gene expression system or vector comprising the fourth polynucleotide of the invention, operatively linked to, at least, one promoter which directs the transcription of said sequence of nucleotides, and to other sequences necessary or appropriate for the transcription and their suitable regulation in time and place, for example, initiation and termination signals, cleavage sites, polyadenylation signals, replication origin, transcriptional enhancers, transcriptional silencers, etc.

In another aspect of the invention a genetic construction of DNA or RNA is provided, hereinafter fifth genetic construction of the invention, comprising one of the following types of sequences:

a) sequence of nucleotides, comprising, at least, the eleventh polynucleotide of the invention, or the coding sequence of SEQ ID NO: 50, for its transcription in vitro or in vivo, or b) sequence of nucleotides, corresponding to a gene expression system or vector comprising the eleventh polynucleotide of the invention, operatively linked to, at least, one promoter which directs the transcription of said sequence of nucleotides, and to other sequences necessary or appropriate for the transcription and their suitable regulation in time and place, for example, initiation and termination signals, cleavage sites, polyadenylation signals, replication origin, transcriptional enhancers, transcriptional silencers, etc.

In another aspect of the invention a genetic construction of DNA or RNA is provided, hereinafter sixth genetic construction of the invention, comprising one of the following types of sequences:

a) sequence of nucleotides, comprising the fifth polynucleotide of the invention, or b) sequence of nucleotides, comprising the sixth polynucleotide of the invention, operatively linked to a gene of interest. Said construction enables directing the expression of the gene of interest specifically in axillary buds.

A great number of these constructions, systems or expression vectors may be obtained by conventional methods known by persons skilled in the art and form part of the present invention.

A "vector" is a replicon, or an integrative vector, whereto another polynucleotide segment has been linked, to perform the replication and/or expression of the linked segment.

A "replicon" is any genetic element which behaves as an autonomous unit of polynucleotide replication within a cell; i.e. capable of replicating under its own control.

An integrative vector is any genetic element which is integrated and maintains stable in the cell genome.

"Control sequence" relates to polynucleotide sequences necessary to carry out the expression of the sequences whereto they are linked. The nature of said control sequences differs depending on the host organism; in prokaryotes, said control sequences generally include a promoter, a ribosomal binding site and termination signals; in eukaryotes, generally, said control sequences include promoters, termination signals, intensifiers and, on occasions, silencers. It is aimed that the term "control sequences" includes, at minimum, all the components whose presence is necessary for expression and it can also include additional components whose presence is advantageous.

As used here, the term "promoter" refers to a region of the DNA upstream from the start point of the transcription, and particular therein, which is capable of initiating the transcription in a plant cell, whether the origin of the promoter is a plant or not. Examples of promoters include, but are not limited to, promoters obtained from plants, plant virus, and bacteria that may express genes in plant cells, such as *Agrobacterium* or *Rhizobium*. Examples of promoters under the control of development include promoters that preferably initiate transcription in certain tissues, such as leaves, roots or seeds. Said promoters are denominated in this specification as preferable of a type of tissue. There are other promoters which initiate transcription in a certain type of tissues, and are called "specific tissues". An "inducible" or "repressible" promoter is a promoter which is under the control of the environment. Examples of environmental conditions that may affect transcription are anaerobic conditions, or the presence of light. The promoters of specific tissue, preferred tissue, specific of a cell type or inducible promoters are types that constitute the class of "non-constitutive" promoters the class of "non-constitutive" promoters. A "constitutive" promoter is a promoter which is active in the majority of environmental conditions.

"Operatively linked" relates to a juxtaposition wherein the components thus described have a relation that allows them to operate in the intended manner. A control sequence "operatively linked" to a sequence which transcribes the nucleotide sequence of the invention is linked so that the expression of the encoding sequence is achieved in conditions with the control sequences.

An "encoding sequence" or "coding sequence" is a sequence of polynucleotides which is transcribed to mRNA and/or is translated into a polypeptide when it is under the control of suitable regulating sequences. The limits of the coding sequence are determined by a translation initiation codon at end 5' and a translation termination codon at end 3'. A coding sequence may include, but is not limited to, mRNA, cDNA, and recombinant polynucleotide sequences.

The terms "polynucleotide" and "nucleic acid" are used here interchangeably, referring to polymeric forms of any length, both ribonucleotides (RNA) and deoxyribonucleotide (DNA).

The terms "amino acid sequence", "peptide", "oligopeptide", "polypeptide" and "protein" are used here interchangeably, and refer to a polymeric form of amino acids of any length which may or may not be chemically or biochemically modified.

Another aspect of the invention relates to the use of the polynucleotides of the invention, or the genetic constructions of the invention, in the production of cells and transgenic plants which have a modified plant architecture.

In this specification "plant architecture" is understood as the sum of the observable structural properties of an organism (plant), for example, the trend of the plants to grow vertically or shrub-like, together with the functional properties that constitute the phenotype of said organism, which is the result of the interaction between the genotype and the environment.

"Plant" in this specification is understood to be all organisms that can be classified within the kingdom Viridiplantae, including green algae and land plants (Embryophyta).

The organisms of the genus *Solanum* belong to the Superkingdom Eukaryota, Kingdom Viridiplantae, Phylum Streptophyta, Subclass Asteridae, Orden Solanales, Family Solanaceae. *Solanum tuberosum* is the scientific name of the potato plant, and *Solanum lycopersicum* that of the tomato plant.

In another aspect of the invention a method is provided to modify the plant architecture of a plant, comprising:

a) transfecting the polynucleotides or the genetic constructions of the invention in a cell or culture of host plant cells, b) growing the cell or the culture of host plant cells in a suitable medium, until regenerating a complete plant.

A "host" or "host cell" as used in this specification relates to an organism, cell or tissue, particularly to a plant cell, which serves as target or recipient of the transfected elements (for example, the polynucleotides or the genetic constructions of the invention). A host cell may also indicate a cell or host that expresses a recombinant protein of interest (for example, the product of the expression of the polynucleotides of the invention) where the host cell is transformed with an expression vector containing the polynucleotides of the invention or also the promoters of the invention which direct the expression of a gene of interest.

"Transfecting" or "transgenesis" in this specification is understood as the process of transferring foreign DNA to an organism, which becomes in this way known as "transgenic".

The term "transgenic" is used in the context of the present invention to describe plants wherein a foreign sequence of DNA has been incorporated stably, and in particular the polynucleotides or the genetic constructions of the invention.

In a preferred embodiment of this aspect of the invention, the cell, the culture of plant cells and/or the plant may be taxonomically classified in the species *Solanum tuberosum* L. In a preferred embodiment of this aspect of the invention, the cell, the culture of plant cells and/or the plant may be taxonomically classified in the species *Solanum lycopersicum*.

The method to modify the plant architecture of a plant provided by the invention comprises any process of plant transformation wherein the allogenous elements introduced comprise the polynucleotides of the invention or the genetic constructions of the invention.

In another aspect of the invention a method is provided to express a gene of interest in the axillary meristems of a plant comprising:

a) transfecting the polynucleotides or the genetic constructions of the invention in a cell or culture of host plant cells, b) growing the cell or the culture of host plant cells in a suitable medium, until regenerating a complete plant.

In a preferred embodiment of this aspect of the invention, the cell, the culture of plant cells and/or the plant may be taxonomically classified in the species *Solanum tuberosum* L. In a preferred embodiment of this aspect of the invention, the cell, the culture of plant cells and/or the plant may be taxonomically classified in the species *Solanum lycopersicum*.

The method to express a gene of interest in the axillary meristems of a plant provided by the invention comprises any process of plant transformation wherein the allogenic elements introduced comprise the polynucleotides of the invention or the genetic constructions of the invention.

The polynucleotides and some of the genetic constructions of the present invention are expressed in temporally and spatially regulated form (for example, in certain stages of development and in certain tissues, axillary buds) and at controlled levels. An aspect of the present invention consists of altering (increasing or decreasing) said expression levels.

The present invention also comprises modulating agents of the expression of the proteins coded by the polynucleotides of the invention, and/or of the genes constituting coding for these proteins in the tomato plant and the potato (SlBRC1L1, SlBRC1L2, StBRC1L1 and StBRC1L2). With the development of anti-sense technology, sequences of specific nucleotides complementary to a certain sequence of DNA or RNA, could form complexes and block the transcription or translation. Furthermore, with the progress of post-transcriptional gene silencing and, in particular, interfering RNA (or RNAi), tools have been developed which allow the specific inhibition of the expression of a gene. The inhibition of the expression of the genes SlBRC1L1, SlBRC1L2, StBRC1U and StBRC1L2 would hence constitute the inhibition of its biological activity, allowing the modulation of said activity in the plant.

In the context of the present invention, SlBRC1L1 is defined by a sequence of nucleotides or polynucleotide, which constitutes the coding sequence of the protein SlBRC1L1, and would comprise different variants of:

a) nucleic acid molecules which code for a polypeptide comprising the amino acid sequence of SEQ ID NO: 1, or the amino acid sequence of SEQ ID NO: 50, b) nucleic acid molecules the complementary chain whereof hybridizes with the polynucleotide sequence of a), c) nucleic acid molecules the sequence whereof differs from a) and/or b) due to the degeneration of the genetic code, d) nucleic acid molecules which code for a polypeptide comprising the amino acid sequence with an identity of at least 95%, 98% or 99% with the SEQ ID NO: 1 or with the SEQ ID NO: 50, wherein the polypeptide coded by said nucleic acids have the activity and the structural characteristics of the protein SlBRC1L1.

A nucleotide sequence capable of being translated into SEQ ID NO: 1 could be, but without being limited to, the sequence included in SEQ ID NO: 7.

In the context of the present invention, SlBRC1L2 is defined by a sequence of nucleotides or polynucleotide, which constitutes the coding sequence of the protein SlBRC1L2, and would comprise different variants from:

a) nucleic acid molecules which code for a polypeptide comprising the amino acid sequence of SEQ ID NO: 2, b) nucleic acid molecules the complementary chain whereof hybridizes with the polynucleotide sequence of a), c) nucleic acid molecules the sequence whereof differs from a) and/or b) due to the degeneration of the genetic code, d) nucleic acid molecules which code for a polypeptide comprising the amino acid sequence with an identity of at least 95%, 98% or 99% with the SEQ ID NO: 2, wherein the polypeptide coded by said nucleic acids have the activity and the structural characteristics of the protein SlBRC1L2.

A nucleotide sequence capable of being translated into SEQ ID NO: 2 could be, but without being limited to, the sequence included in SEQ ID NO: 8.

In the context of the present invention, StBRC1L1 is defined by a sequence of nucleotides or polynucleotide, which constitutes the coding sequence of the protein StBRC1L1, and would comprise different variants of:

a) nucleic acid molecules which code for a polypeptide comprising the amino acid sequence of SEQ ID NO: 3, b) nucleic acid molecules the complementary chain whereof hybridizes with the polynucleotide sequence of a), c) nucleic acid molecules the sequence whereof differs from a) and/or b) due to the degeneration of the genetic code, d) nucleic acid molecules which code for a polypeptide comprising the amino acid sequence with an identity of at least 95%, 98% or 99% with the SEQ ID NO: 3, wherein the polypeptide coded by said nucleic acids have the activity and the structural characteristics of the protein StBRC1L1. A nucleotide sequence capable of being translated into SEQ ID NO: 3 could be, but without being limited to, the sequence included in SEQ ID NO: 9.

In the context of the present invention, StBRC1L2 is defined by a sequence of nucleotides or polynucleotide, which constitutes the coding sequence of the protein StBRC1L2, and would comprise different variants of:

a) nucleic acid molecules which code for a polypeptide comprising the amino acid sequence of SEQ ID NO: 4, b) nucleic acid molecules the complementary chain whereof hybridizes with the polynucleotide sequence of a), c) nucleic acid molecules the sequence whereof differs from a) and/or b) due to the degeneration of the genetic code, d) nucleic acid molecules which code for a polypeptide comprising the amino acid sequence with an identity of at least 95%, 98% or 99% with the SEQ ID NO: 4, wherein the polypeptide coded by said nucleic acids have the activity and the structural characteristics of the protein StBRC1 L2.

A nucleotide sequence capable of being translated into SEQ ID NO: 4 could be, but without being limited to, the sequence included in SEQ ID NO: 10.

Furthermore, due to the existence of different alleles, the amino acid sequence whereinto the gene StBRC1L2 is translated may vary, being included in an alternative sequence in SEQ ID NO: 51. A nucleotide sequence capable of being translated into SEQ ID NO: 51 could be, but without being limited to, the sequence included in SEQ ID NO: 52.

"Antisense polynucleotides" are understood to be chains of ribonucleotides or deoxyribonucleotides which may inhibit the activity of these genes by one of these two mechanisms:

1—Interfering the transcription, on hybridizing with the structural gene or in a regulator or promoter region of the gene which codes for these transcription factors (SlBRC1L1, SlBRC1L2, StBRC1L1 and StBRC1L2). Since the transcription or expression is effectively blocked by the hybridization of the antisense oligonucleotide with the DNA, the production of these transcription factors decreases.

2—The linking of the antisense oligonucleotide in the cytoplasm with the mRNA, interfering with the formation of the actual translation complex, inhibiting complex of translation, inhibiting the translation of the mRtoA into protein.

The post transcriptional gene silencing, and in particular of the interfering RNA also give rise to less production of these transcription factors. The interfering RNA or interfering RNA (or iRNA), is a molecule of RNA which causes the degradation of the RNA of specific genes. In this specification, the interfering RNA includes both the siRNA (small interfering RNA, and the tsRNA ("trans-splicing RNA"), VIGS ("Virus induced gene silencing") and the miRNA or microARN. The siRNA are double strands of RNA, perfectly complementary, of approximately 20-21 nucleotides (nt) with 2 free nucleotides at each end 3'.

Each strand of RNA has a phosphate 5' group and a hydroxyl (—OH) 3' group. This structure comes from the processing carried out by Dicer, an enzyme which cuts long strands of double strand (dsRNA) in siRNAs. One of the strands of the siRNA (the antisense) is assembled in a protein complex called RISC (RNA-induced silencing complex), which uses the strand of siRNA as guide to identify the complementary messenger RNA. The RISC complex catalyzes the cleavage of the complementary mRNA in two halves, which are degraded by the cellular machinery, thus blocking the gene expression. The miRNAs are small interfering RNAs which are generated from specific precursors coded in the genome, which on being transcribed is folded in intramolecular hairpins which contain segments of imperfect complementarity. The processing of the precursors generally occurs in two stages, catalysed by two enzymes, Drosha in the nucleus and Dicer in the cytoplasm. One of the strands of the miRNA (the antisense), as occurs with the siRNAs, is incorporated in a complex similar to the RISC. Depending on the degree of complementary of the miRNA with the mRNA, the miRNAs may either inhibit the translation of the mRNA or induce their degradation. However, unlike the pathway of the siRNAs, the degradation of mRNA mediated by miRNAs starts with the enzymatic elimination of the poly-A tail of the mRNA.

Therefore, it could be any siRNA or miRNA capable of hybridizing a nucleic acid molecule which codes these transcription factors (SlBRC1L1, SlBRC1L2, StBRC1L1 and StBRC1L2), or an RNA construction which at least contains any of the possible sequences of siRNA or miRNA nucleotides capable of inhibiting the translation of the orthologous proteins of BRC1 of the invention, and without prejudice to additionally forming part of the present invention any of the sequences and RNA constructions of the invention mentioned above which are object of modifications, preferably chemical, which lead to a greater stability against the action of ribonuclease and with this a greater efficiency. Without said modifications supposing the alteration of its mechanism of action, which is the specific link to the RISC complex (RNA-induced silencing complex), activating it and manifesting a helicase activity which separates the two strands leaving only the antisense strand associated to the complex.

Additionally, it is evident for a person skilled in the art that a great quantity of mRNA polynucleotides may be translated into proteins SlBRC1L1, SlBRC1L2, StBRC1L1 and StBRC1L2 as a consequence, for example, of the genetic code being degenerated. Any siRNA or miRNA capable of inhibiting the translation of these mRNA also form part of the invention.

The authors of the present invention have developed four sequences of interfering RNA, two of them aimed at reducing the mRNA levels of the genes SlBRC1L1 and SlBRC1L2 of the tomato plant (seventh—SEQ ID NO: 11—and eighth—SEQ ID NO: 12—polynucleotide of the invention, respectively) and two of them aimed at reducing the mRNA levels of the genes StBRC1L1 and StBRC1L2 of the potato (ninth and tenth polynucleotide of the invention, SEQ ID NO: 13 and SEQ ID NO: 14 respectively). Therefore, another aspect of the invention relates to a sequence which is selected from the list comprising SEQ ID NO: 11, SEQ ID NO: 12, SEQ ID NO: 13 or SEQ ID NO: 14.

The sequences of interfering RNA of the invention would serve to modify the plant architectures of the plants, and in particular of the tomato plant and of the potato. As demonstrated in the examples of the present invention, the inhibition of the SlBRC1L1 gene of the tomato plant does not produce an apparent modification (with respect to the elongation of the aerial branches) of the plant architecture (or of its phenotype). This is indicative that, although both genes control the branching, each one has a certain degree of specialization and functional divergence so that in the tomato plant, SlBRC1L2 could have a more important than SlBRC1L1 in the control of branch elongation. On the other hand, in the potato plant, StBRC1 L1 would preferably control the branching of the stolons and StBRC1L2 the elongation of aerial branches.

A genetic construction of DNA also forms part of the present invention, which would direct the in vitro or intracellular transcription of the sequence of siRNA, miRNA, or RNA construction of the invention, and comprising, at least, one of the following types of sequences: a) sequence of DNA nucleotides, preferably double chain, comprising, at least, the sequence of the siRNA or miRNA of the invention or of the RNA construction of the invention for its transcription, or, b) sequence of DNA nucleotides, preferably double chain, corresponding to a gene expression system or vector comprising the sequence which transcribes to the RNA sequence of the invention operatively linked to, at least, one promoter which directs the transcription of said sequence of nucleotides of interest, and to other sequences necessary or appropriate for the transcription and their suitable regulation in time and place, for example, initiation and termination signals, cleavage sites, polyadenylation signals, replication origin, transcriptional enhancers, transcriptional silencers, etc. Said genetic construction could be used in the modification of the plant architecture. Many of these constructions, systems or expression vectors can be obtained by conventional methods known by persons skilled in the art (Sambrook et al. 2001. Molecular Cloning: A Laboratory Manual. Cold Spring Harbor Laboratory Press, New York). Examples of these constructions would be, but without being limited to, the binary DNA plasmids used for the generation of the lines 35SCaMV:: SlBRC1L1 RNAi, 35SCaMV:: SlBRC1L2 RNAi, 35SCaMV:: StBRC1L1 RNAi and 35SCaMV:: StBRC1L2 RNAi, and which are included in FIG. 7 of this specification.

The preparation of other siRNA or miRNA sequences of the invention or of the RNA constructions of the invention would be evident for a person skilled in the art, and could be carried out by chemical synthesis, which also permits the incorporation of chemical modifications both in the different nucleotides of the product and the incorporation of other chemical compounds at any of the ends. On the other hand, the synthesis could also be performed enzymatically using any of the available RNA polymerases. The enzymatic synthesis also allows chemical modifications of the products or inhibitor RNAs.

The design of the siRNA or miRNA nucleotide sequences of the invention would also be evident for a person skilled in the art. Thus, for the siRNA it could be performed by a random design wherein 19-25 bases of the target mRNA are selected without bearing in mind the sequence or the positional information it has in the transcript. Another non-limiting alternative of the present invention would be the conventional design by simple parameters developed by the pioneers of the technique (Calipel et al., 2003. *J Biol. Chem.* 278(43): 42409-12418) completed with BLAST analysis of nucleotides. Another possibility could be a rational design wherein a computer process is used aimed at identifying the optimum targets of siRNA in a mRNA. The target sequences are analysed in groups of 19 nucleotides at the same time and are identified as those which have the best characteristics depending on an algorithm which incorporates a great number of thermodynamic and sequence parameters.

The antibodies capable of linking to proteins SlBRC1L1, SlBRC1L2, StBRC1L1 and StBRC1L2 can be used to inhibit the activity of said proteins, therefore modulating said activity. Therefore, in another preferred embodiment of this aspect of the invention, the modulating agent is selected from antibodies, fragments thereof, or any of their combinations. The antibodies may be polyclonal (typically include different antibodies directed against different determinants or epitopes) or monoclonal (directed against a single determinant in the antigen. The monoclocal antibody may be altered biochemically, by genetic manipulation, or may be synthetic, lacking, possibly, the antibody in its totality or in parts, of portions which are not necessary for the recognition of the proteins SlBRC1L1, SlBRC1L2, StBRC1L1 and StBRC1L2 and being substituted by others which communicate additional advantageous properties to the antibody. The antibody may also be recombinant, chimerical, synthetic or a combination of any of the previous.

The term "antibody" as used in this specification, relates to molecules of immunoglobulins and immunological active portions of immunoglobulin molecules, i.e. molecules that contain an antigen fixation site which is specifically bound (immunoreactance) with the proteins SlBRC1L1, SlBRC1L2, StBRC1L1 and StBRC1L2. Examples of portions of immunologically active immunoglobulin molecules include fragments F(ab) and F(ab')2 which may be generated by treating the antibody with an enzyme such as pepsin. It may be a monoclonal or polyclonal antibody.

A "recombinant antibody or polypeptide" (rAB) is one which has been produced in a host cell which has been transformed or transfected with the coding nucleic acid of the polypeptide, or produces the polypeptide as a result of homologous recombination.

These rAC can be expressed and directed towards specific cellular subcompartments when the appropriate sequences for intracellular traffic are incorporated. These antibodies are called intrabodies, and have demonstrated their efficacy not only to deviate proteins from their habitual compartment or block interactions between proteins involved in signalling pathways, but also to activate intracellular proteins.

Part of the invention is also the genetic constructions of DNA capable of transcribing to a peptide, antibody or fragment of antibody, for their use in a modification of the plant architecture. Said genetic construction of DNA would direct the in vitro or intracellular transcription of the sequence of the antibody or fragment thereof, and comprises, at least, one of the following types of sequences: a) sequence of DNA nucleotides, preferably double chain, comprising, at least, the coding sequence of the antibody of the invention or of the fragment of antibody of the invention for its in vitro or intracellular transcription, b) sequence of DNA nucleotides, preferably double chain, corresponding to a gene expression system or vector comprising the coding sequence of the sequence of antibody or fragment of antibody of the invention operatively linked to, at least, one promoter which directs the transcription of said sequence of nucleotides of interest, and to other sequences necessary or appropriate for the transcription and their suitable regulation in time and place, for example, initiation and termination signals, cleavage sites, polyadenylation signals, replication origin, transcriptional enhancers, transcriptional silencers, etc. for their use in the modification of the plant architecture.

Ribozymes could also be used as modulating agents of the activity of the proteins SlBRC1L1, SlBRC1L2, StBRC1L1 and StBRC1L2. A "ribozyme" as understood in the present invention, relates to a catalytic polynucleotide (typically RNA), which may be built to specifically recognize, by hybridization, a mRNA and fragment it or eliminate its expression. The ribozymes may be introduced in the cell as catalytic RNA molecules or as genetic constructions which are expressed to catalytic molecules of RNA.

The compositions comprising the antisense oligonucleotides antisense (siRNA, miRNA or the RNA construction), the antibodies, or the genetic constructions modulating the expression of the genes SlBRC1L1, SlBRC1L2, StBRC1L1 and StBRC1L2 of the invention also form part of the invention. The compositions of the present invention allow the transfection of the siRNA, miRNA or the RNA construction of the invention to the interior of a cell, in vivo or in vitro. The transfection could be carried out, but without being limited to, direct transfection or vectors that facilitate the access of the siRNA, miRNA or the RNA construction to the interior of the cell. Thus, examples of these vectors are, without being limited to, virus, non-viral binary plasmids of DNA, and molecular conjugates. Thus, for example, the siRNA of the present invention, as well as RNA or DNA precursors of these siRNA, miRNA or RNA constructions can be conjugated with release peptides or other compounds to favour the transport of these RNA to the interior of the cell.

Another aspect relates to a seed, hereinafter seed of the invention, the genetic material whereof integrates the isolated polynucleotides of the invention (including also the modulating agents, such as for example, but without being limited to, those set down in SEQ ID NO: 11, SEQ ID NO: 12, SEQ ID NO: 13 and SEQ ID NO: 14) or the genetic constructions of the invention. In a preferred embodiment, the seed of the invention can be taxonomically classified as belonging to the species Solanum tuberosum L. In a preferred embodiment, the seed of the invention can be taxonomically classified as belonging to the species Solanum lycopersicum.

Another aspect relates to a plant cell, hereinafter plant cell of the invention, the genetic material whereof integrates the isolated polynucleotides of the invention or the genetic constructions of the invention. Preferably, the plant cells of the invention can be taxonomically classified as belonging to the species Solanum tuberosum L. In another preferred embodiment, it can be taxonomically classified as belonging to the species Solanum lycopersicum.

Another aspect relates to a culture of plant cells, hereinafter culture of plant cells of the invention, the genetic material whereof integrates the isolated polynucleotides of the invention or the genetic constructions of the invention. Preferably, the plant cells of the culture of the invention may be taxonomically classified as belonging to the species Solanum tuberosum L. In another preferred embodiment, they may be taxonomically classified as belonging to the species Solanum lycopersicum.

The term "culture of cells" in this specification, refers to a culture of cells isolated therefrom or a different type of tissue, or a collection of said cells organized in parts of a plant or in tissues (tissue cultures). Types of cultures of this type are, for example, cultures of protoplasts, calluses (groups of undifferentiated plant cells capable of regenerating a complete plant) and plant cells which are isolated from plants or parts of the plants, such as embryos, protoplasts, meristematic cells, pollen, leaves or anthers.

Another aspect of the invention relates to a group of cells, which may be taxonomically classified as belonging to the species Solanum tuberosum L the genetic material whereof integrates the isolated polynucleotides of the invention or the genetic constructions of the invention, and which form the tubers, the minitubers or the microtubers.

"Minitubers", or "papa seed" are known as small tubers of no more than 3 cm diameter used to perform the large commercial plantations of potato crops. Failing this, medium-sized tubers are used or parts of them which have at least one eye (i.e. a bud).

Another aspect relates to a plant, hereinafter plant of the invention, comprising the cells or the culture of plant cells of the invention, and/or which has been obtained after the growth of the seed of the invention. Said plant would integrate in its genetic material the polynucleotides of the invention, and/or the genetic constructions of the invention. Preferably, the plant cells of the culture of the invention may be taxonomically classified as belonging to the species Solanum tuberosum L. In another preferred embodiment, they may be taxonomically classified as belonging to the species Solanum lycopersicum.

Modifications in the genes SlBRC1L1, SlBRC1L2, StBRC1L1 and StBRC1L2, would therefore allow modifying the plant architecture of a plant. Since in this invention it includes the sequence of these genes, as well as the respective proteins into which they are translated, the obtainment of plants whose plant architecture is modified could be done by several methods.

By selection of spontaneous mutants: it must bear in mind that in each cellular division there is a small probability that a genetic change occurs, for which reason it is not surprising that in a great cell mass the population is heterogeneous. This distribution may have problems of yield since, in general, the variants have less production levels than the parent population. These definitive changes (mutations) must be distinguished from the phenotypical variations that depend on the environmental conditions and which take place in the population that expresses the same physiological modification, within the variations permitted by its genotype. In spontaneous mutations, if the responsible element of the mutation is not known, it is very difficult to differentiate these phenotypical variations from those which have modifications in the genes responsible for the plant architecture and which are stables and hereditary. The present invention provides the necessary tools to carry out a selection of those mutants not only by the observation of the morphological characteristics of interest, but also by the detection of mutations in the genes responsible for said mutations (SlBRC1L1, SlBRC1L2, StBRC1L1 and StBRC1L2), designing a simple selective screening process for a particular type of mutants. For example, those plants could be morphologically selected, preferably the tomato plant or the potato, which have an advantageous plant architecture, and to later check if the genes SlBRC1L1, SlBRC1L2, StBRC1L1 and StBRC1L2 have mutations with respect to a control wild genotype. Therefore, another aspect of the invention relates to a tomato plant, a fruit, seed, cells, group of cells or parts of the plant, which have a plant architecture modified with respect to the control-type tomato plants, where the modification of the plant architecture is due to non-transgenic mutations in the genes SlBRC1L1 and SlBRC1L2 of tomato.

Another aspect of the invention relates to a potato plant, a fruit, seed, cells, group of cells or parts of the plant, which have a plant architecture modified with respect to the control-type potato plants, where the modification of the plant architecture is due to non-transgenic mutations in the genes StBRC1L1 and StBRC1L2 of the potato plant.

The term "genotype", as used in this specification, refers to the hereditary or genetic constitution of an individual; all the genetic material contained in a cell, whereto, in general, is called nuclear material.

The term "phenotype", as used in this specification, relates to the sum total of the observable structural and functional properties of an organism product of the interaction between the genotype and the environment.

The term "type" refers to the plant designated as the type of a genus, subgenus, species, variety or another taxonomic category, the "type" being, from a taxonomic standpoint, the simple element of a taxon whereto the name is permanently assigned and whereon are based the descriptive characteristics which meet the conditions of availability or of valid publication. This specification also describes a tomato or potato control plant with which other plants of the same taxonomic category are compared to observe if its plant architecture has been modified, to later analyse if the genes SlBRC1L1 and SlBRC1L2 (in the tomato plant) and StBRC1L1 and StBRC1L2 (in the potato) have mutations with respect to the genes of the control plant. In this way, it is possible to distinguish the modifications in the plant architecture which are due to physiological, environmental or another type of factors, against those caused by mutations in the genes SlBRC1L1 and SlBRC1L2 (in the tomato plant) and StBRC1 L1 and StBRC1L2.

The induced mutation process involves two stages, the treatment of the population with the chosen mutagen and then the isolation of the mutants for their later testing and selection. Inducing mutations in a plant is a very valuable tool for the improvement of plants, especially when it is desired to improve one or two easily identifiable characteristics in a well-adapted species or variety. Furthermore, it has the advantage that the variability caused by the induced mutations is not essentially different from that caused by spontaneous mutations during the evolution. The choice of a mutagenic agent depends in general on practical considerations. In some of the cases it is more convenient to use more than one instead of the mass use of just one. Until where the isolation of the mutant is possible the improved character thereof must be used (the plant architecture of interest) as selection factor. The mutagenic agents may be grouped in physical (ultraviolet light, x-rays, gamma rays, beta radiation, rapid neutrons, heavy ion beams) and chemical. Most of the chemical mutagens belong to the group of the alkylation agents (ethyl methanesulfonate (EMS), diethyl sulfate (dES), . . . ) but there are other groups, such as analogues of bases (such as 5-bromouracil and 2-aminopurine) and structural mutagens (such as proflavin or acridine orange).

Mutagens principally create isolated mutagens and small deletions, insertions, transversions and/or transitions (of around 1 to 5 nucleotides). For example, but without limiting ourselves, they could be mutagens such as methylmethane sulfonate (MMS), Nitrosoguanidine (NTG), N-ethyl-N-nitrosourea (ENU), triethylmelamine (TEM), N-methyl-N-nitrosourea (MNU), procarbazine, chlorambucil, cyclophosphamide, diethyl sulphate, acrylamide monomer, melphalan, vincristine, dimethylnitrosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, busulfan, diepoxyalkanes (diepoxyoctane (DEO), diepoxybutane (BEB), 2-methoxy-6-chloro-9[3-(ethyl-2-chloro-ethyl)aminopropylamine]acridine dihydrochloride (ICR-170), formaldehyde, etc.

Thus, for example, the seeds are subjected to the action of chemical mutagens, which give rise to a series of mutagens in the genome of said seeds. Said seeds grow giving rise to adult plants (M1), which self-pollinate giving rise to generation M2. The DNA of the M2 plants is subjected to a screening to see if it has mutations in the gene of interest. Once the mutation has been identified in the gene of interest, the seeds of the M2 plants carrying said mutation grow, giving rise to M3 plants, which are subjected to a screening to see it they manifest the phenotypical characteristics associated with the gene of interest.

A person skilled in the art understands that a variety of plant material may be subject to the mutagenesis process, including, but without being limited to, seeds, pollen, cells or tissues of the plant. The type of plant material which is subjected to mutagenesis modifies the stage in the DNA of the plants is subjected to screening to find the mutation. Thus, for example, when the pollen is subjected to mutagenesis before the pollination of a plant, the resulting seeds give rise to M1 plants. Each cell of said M1 plants may contain the mutations induced in the pollen, for which reason it is necessary to wait for the M2 generation to perform the screening. This process is known in the state of the art as tilling.

Thus, another aspect of the invention relates to a method for obtaining tomato plants with modified plant architecture, in comparison with the wild control plant, comprising:

a) obtaining plant material from a tomato plant (parent),
b) subjecting the plant material of step (a) to a mutagenesis process
c) culturing the mutated plant material until regenerating a complete plant, and its descendants,
d) analysing the descendants of the plants of step (c) to detect at least one mutation in at least one copy the orthologous genes of BRC1 (genes SlBRC1L1 and SlBRC1L2),
e) selecting the descendants with at least one mutation in at least one copy of the genes SlBRC1L1 and SlBRC1L2 which have their plant architecture modified in comparison with a control type plant,
f) optionally, culturing the plant selected to obtain descendants which have said modification of the plant architecture.

In a preferred embodiment of this aspect of the invention, the mutation is produced in at least one copy of the gene SlBRC1L2. In another preferred embodiment, the induction of the mutation of step (b) is performed by chemical mutagens.

Another aspect of the invention relates to a method for obtaining potato plants with modified plant architecture, in comparison with the wild control plant, comprising:

a) obtaining plant material from a potato plant (parent),
b) subjecting the plant material of step (a) to a mutagenesis process
c) culturing the mutated plant material until regenerating a complete plant, and its descendants,
d) analysing the descendants of the plants of step (c) to detect at least one mutation in at least one copy the orthologous genes of BRC1 (genes StBRC1L1 and StBRC1L2),
e) selecting the descendants with at least one mutation in at least one copy of the genes StBRC1 L1 and StBRC1 L2 which have their plant architecture modified in comparison with a control type plant,
f) optionally, culturing the plant selected to obtain descendants which have said modification of the plant architecture.

In a preferred embodiment of this aspect of the invention, the induction of the mutation of step (b) is performed by chemical mutagens.

Throughout the description and the claims the word "comprises" and its variants are not intended to exclude other technical characteristics, additives, components or steps. For persons skilled in the art, other objects, advantages and characteristics of the invention will be inferred in part from the description and in part from the practice of the invention. The following figures and examples are provided by way of illustration, and are not intended to limit the present invention.

EXAMPLES

Figure 1:
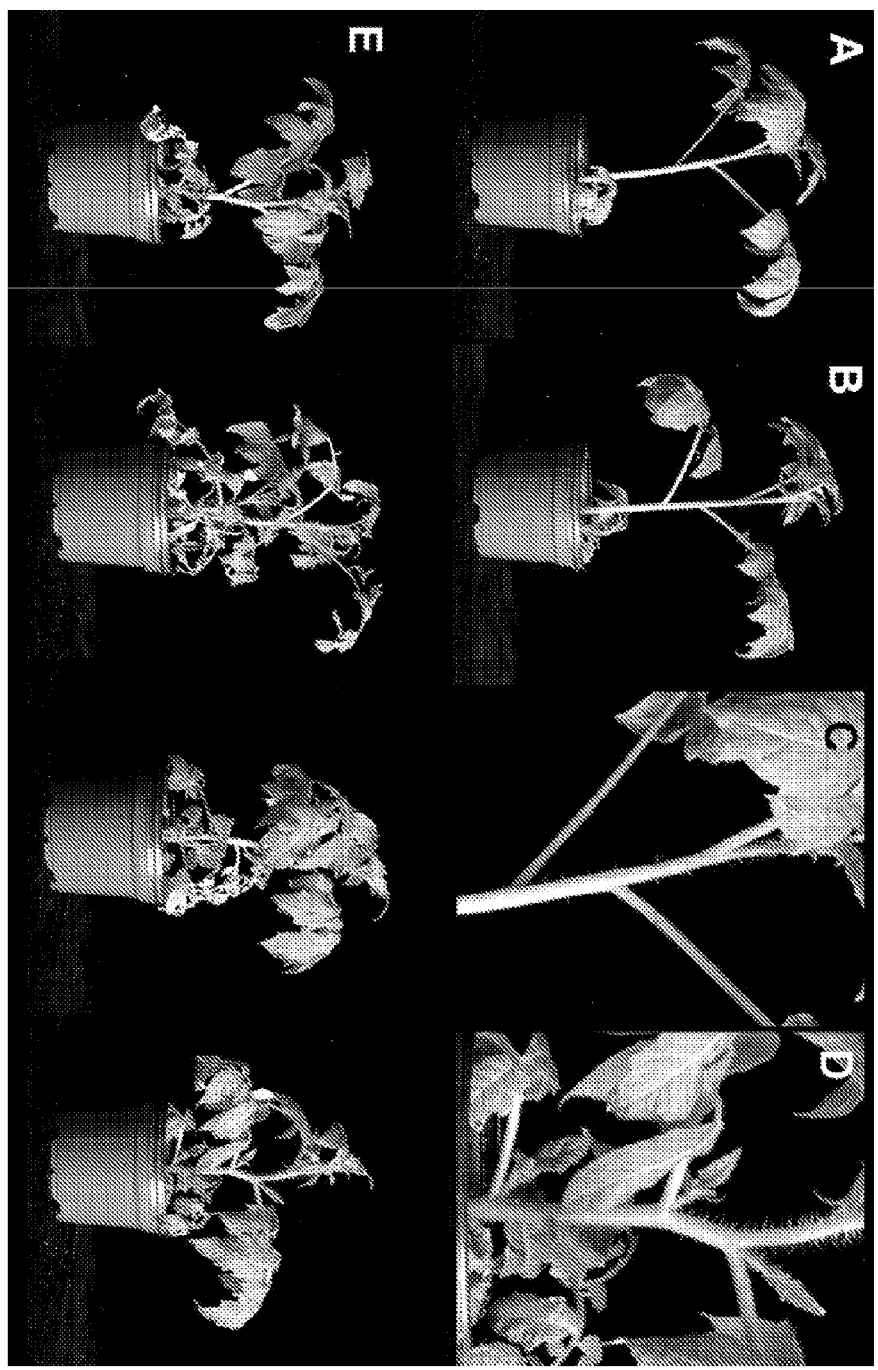
FIG. 1. Phenotype of the transgenic tomato lines with reduced activity of the genes SlBRC1L1 and SlBRC1L2. General aspect of the Moneymaker variety control plant (A) and line 35SCaMV::SlBRC1L1 RNAi (B). Detail of axillary bud of control plant (C) and of plant 35SCaMV:: SlBRC1L2 RNAi (D). E. General aspect of plants of lines 35SCaMV:: SlBRC1L2 RNAi.
Figure 2:
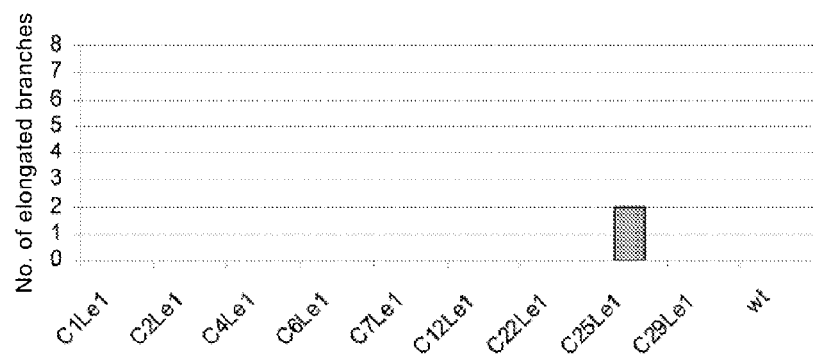
FIG. 2. Quantification of the plant branching phenotype of the control tomato plant, lines 35SCaMV:: SlBRC1L1 RNAi (A) and 35SCaMV:: SlBRC1L2 RNAi (B).
Figure 2:
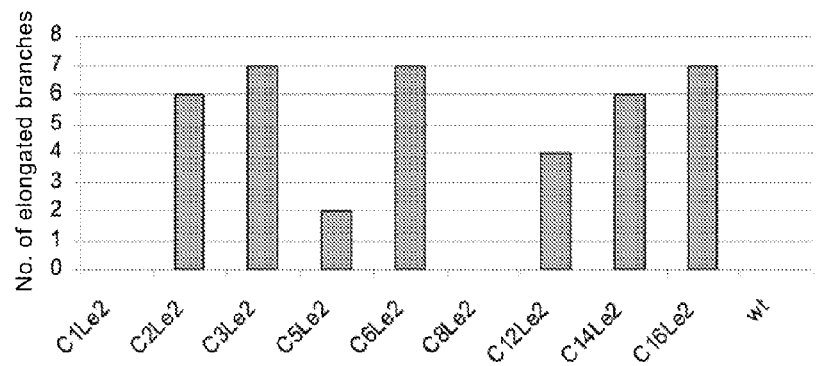

The invention will be illustrated below by assays performed by the inventors, which reveal the specificity and efficacy of the modifications in the expression of the genes SlBRC1L1, SlBRC1L2, StBRC1L1 and StBRC1L2 in the alteration of the plant architecture of the tomato plant and of the potato plant.

Example 1

Cloning of the Genomic, Promoter and Coding Sequences of the Genes SlBRC1L1 and SlBRC1L2

To clone the orthologues to BRC1 of the tomato plant a search was performed of BRC1-type TCP genes in different databases of solanaceae: TIGR Solanaceae Genomics Resource BLAST page, TIGR Plant Transcript Assemblies Database and SOL Genomics Network. To carry out the comparison, the sequence of amino acids of the TCP box of the BRC1 protein of *Arabidopsis* was used, and an EST (Expressed Sequence Tags) and a cDNA was found whose translation gave rise to proteins with high homology with BRC1 of *arabidopsis*. The EST EST522935 had 447 bp and the partial cDNA AY168167, 415 bp. The nucleotide sequences of the genes SlBRC1L1 and SlBRC1L2 are collected in SEQ ID NO: 7 and SEQ ID NO: 8, respectively.

To amplify the complete cDNAs (SEQ ID NO: 15 for SlBRC1L1 and SEQ ID NO: 16 for SlBRC1L2) of both genes, two different strategies were followed. In the case of SlBRC1L1, two nested primers were designed (Le1, SEQ ID NO: 17 and Le2, SEQ ID NO: 18) in region 5' of the gene, and the complete cDNA was amplified with PCR with oligo dT from cDNA of axillary buds of the tomato plant. In the case of the gene SlBRC1L2, the available sequence included neither end 5' nor 3', for which reason the cloning was performed of both ends by the SMART™ RACE cDNA Amplification Kit (Clontech). By using this kit, synthetic adapters were incorporated at ends 5' and 3' during the synthesis of the cDNA performed from total RNA of axillary buds of the tomato plant. For the amplification of both ends using the sequence of the synthetic adapters, two pairs of nested primers were designed in the available sequence of the gene SlBRC1L2: LeTCP2—F1 (SEQ ID NO: 19) and LeTCP2—F1 nested (SEQ ID NO: 20) for end 3' and LeTCP2-R1 (SEQ ID NO: 21) and LeTCP2—R1 nested (SEQ ID NO: 22) for end 5'. Once the sequence of both overlapping fragments 5' and 3' were obtained primers (LeTCP2 cDNA-F, SEQ ID NO: 23) and LeTCP2 cDNA-R, SEQ ID NO: 24) were designed to amplify the complete gene.

In the case of the gene SlBRC1L1, two types of cDNA were amplified, one with an open long-reading phase (1041 pb) and one with an open short-reading phase (978 pb) by a processing of different introns, whilst in the case of SlBRC1L2 only one type of cDNA was amplified with an open reading phase of 1014 pb. The PCR fragments corresponding to the three cDNAs were cloned in the pGEMT-easy™ vector (Promega).

Once the complete sequence of both genes is known, the fragments corresponding to their genomic sequence was amplified (SEQ ID NO: 7 for SlBRC1L1 and SEQ ID NO: 8 for SlBRC1L2), using primers which included zones 5' and 3' corresponding to each gene: Le1 (SEQ ID NO: 17) and Le3 (SEQ ID NO: 25) to amplify the genomic sequence of SlBRC1L1, and SlBRC1L2 cDNA-F (SEQ ID NO: 23) and LeTCP2 cDNA-R (SEQ ID NO: 24) to amplify that of SlBRC1L2. In the case of SlBRC1L1, on comparing the genomic sequence with that corresponding to the coding zone, the existence of two introns was observed, which were eliminated in the short cDNA, but one of which is maintained in the long cDNA. In the case of the gene SlBRC1L2, the comparison of the genomic sequence with the coding showed the existence of an intron.

The isolation of the promoter zones of both genes (SEQ ID NO: 5 for SlBRC1L1 and SEQ ID NO: 6 for SlBRC1L2) was performed using a Genome Walker™ (Clontech) library of tomato. Using this strategy, from genomic DNA, different Genome Walker™ libraries were created by digestion with different enzymes which produced blunt ends (DraI, EcoRV, PvuII and SspI) and later linkage of synthetic adapters at the ends produced by digestion. From nested primers designed at around 100 bp of the atg of both genes (GSP1-TCP1, GSP2-TCP1—SEQ ID NO: 26 and SEQ ID NO: 27 respectively—for SlBRC1L1 and GSP1-TCP2, GSP2-TCP2—SEQ ID NO: 28 and SEQ ID NO: 29 respectively—for SlBRC1L2) and of those available for the adapters, two fragments of 1.kb and 0.7 kb in size were amplified by PCR, corresponding to the promoting zones of the genes SlBRC1L1 and SlBRC1L2, respectively. Both fragments were cloned in the pGEMT-easy™ vector.

Example 2

Generation of Transgenic Tomato Plants (*Solanum Lycopersicum*, Moneymaker Variety) with Loss of Function of the Genes SlBRC1L1 and SlBRC1L2 Silenced by the RNAi Technique The DNA fragments chosen to perform the RNA interference are situated between the TCP box and the R box, highly conserved areas and characteristic of the TCP genes. Said fragment rings exclusively with the part of the chosen sequence which guarantees that the silencing is specific for each gene separately, SlBRC1L1 and SlBRC1L2.

The fragment used to silence the gene SlSRC7L1 has 225 base pairs, and the sequence is included in SEQ ID NO: 11, and constitutes the seventh polynucleotide of the invention.

The fragment used to silence the gene SlBRC1L2 has 415 base pairs, and the sequence is included in SEQ ID NO: 12, and constitutes the eighth polynucleotide of the invention.

Strategy Used for the Generation of the RNAi Constructions for the Genes SlBRC1L1 and SlBRC1L2.

To obtain the hairpin structure characteristic of the RNAi, the fragment selected was cloned in the pHannibal plasmid (CSIRO), which carried resistance to ampicillin. Said cloning is directed, so that the fragment enters in direction 5'-3' cloning it with the targets BamH I and Cla I, and at 3'-5' at the other end of the intron PDK (742 pb), using the targets Xho I and Kpn I. Therefore, the fragments selected were amplified using primers containing at end 5' the target sequences for the different restriction enzymes to be used (the primer for end 5' of SlBRC1L1 is included in sequence SEQ ID NO: 30, for end 3' of SlBRC1L1 in sequence SEQ ID NO: 31, for end 5' of SlBRC1L2 in sequence SEQ ID NO: 32 and for end 3' of SlBRC1L2 in sequence SEQ ID NO: 33).

Figure 7:
FIG. 7. Maps of the binary plasmids used for the generation of lines 35SCaMV:: SlBRC1L1 RNAi and 35SCaMV:: SlBRC1L2 RNAi (left) and 35SCaMV:: StBRC1L1 RNAi and 35SCaMV:: StBRC1L2 RNAi (right). It indicates the fragments of sense sequence (box A) and antisense sequence (box B) which are cloned separately by the intron of the pyruvate dehydrogenase kinase (PDKintron), constituting the RNAi structure. In front of the sense fragment A there is the 35S promoter of the cauliflower mosaic virus (35S promoter) and as transcription terminator the octopine synthase terminator (OCSter). It also indicates the ends of the T-DNA, LB (left end) and RB (right end) and the position of the gene of neomycin phosphotransferase, which confers resistance to kanamycin (NPTII KanR).

Once the recombinant plasmids have been obtained with the hairpin structure of the RNAi, and checked by sequencing, the cassette was transferred with the pHannibal transgene (3330 pb) cutting with Not I and it was cloned in the site for the same restriction enzyme of the BluescriptII SK+ plasmid. In this way, it was possible to leave to one side of the sequence a SadI site and at the other side a SmaI site, so that by a digestion with both enzymes of the fragments and of the binary plasmid pBIN19 (FIG. 7), both fragments were subcloned giving rise to constructions which have been introduced in the tomato plant (FIG. 7). The choice was made to use this binary plasmid since it has been well-established that the pBIN19 plasmid effectively transforms tomato, giving resistance to kanamycin in bacteria and in plants. The expression of the transgene is directed by the 35S promoter of the cauliflower mosaic virus (CaMV35S) (1346 pb) promoting its constitutive expression, whilst at end 3' of the gene octopine synthase (OCS terminator) (766 pb) is found of *Agrobacterium* which acts as transcription terminator. Once the constructions in *Escherichia coli* have been obtained, a preparation was made of the plasmids used to transform *Agrobacterium tumefaciens* LBA4404. A single colony was selected from the colonies carrying our plasmids, which was used to transform to transform tomato plants.

Transformation of Tomato Plants.

To stably transform tomato plants, the protocol of Ellul et al. (2003) *Theor Appl Genet.* 106(2): 231-8.) was used. Following this protocol, tomato cotyledons were transformed from plants grown in in vitro conditions in Murashige and Skoog medium with vitamins (*Physiol. Plant.* 15:473-497, 1962) supplemented with 2% sucrose. Once the first true leaves were developed, the cotyledons were cut transversally in one or two portions (explants), depending on the size, and they were placed during two days in the dark with the reverse in contact with the preculture medium (PCM), which includes the hormones AIA and kinetin, at a final concentration of 4 mg/l. After 48 hours, the explants were infected by immersing them during 8 minutes in the *Agrobacterium* culture. After eliminating the excess *Agrobacterium*, the explants were placed in the coculture medium (CCM), which has the same composition of hormones as the previous, adding acetosyringone. The explants were incubated with the bacteria during 48 hours in the dark.

Having concluded the coculture period, the explants were cleaned in washing medium (WM) plus the antibiotic claforan (500 mg/l) to eliminate the *Agrobacterium*, and they were dried on sterile filter paper to pass them to recovery medium (RM) without selective pressure (AIA/Kinetin/Claforan). In this medium, they were cultured in light for two days, after which they were transferred to the first selective medium (SM) whereto another hormone was added, zeatin (1 mg/l) and the antibiotic of selection of the transgene kanamycin (50 mg/l). The explants were cultured in this selective medium until the first change to fresh medium (with the same composition) after three weeks. Calluses were developed from these explants which passed through four three-week subcultures before developing the first apices.

Once the apices were well-developed, the calluses were cut and they were transferred to rooting medium (RM), which includes AIA in low concentration (0.1 mg/l) to favour root development. Once they were well developed, the tomato plants were transferred to a mixture of peat and vermiculite 3:1, maintaining the plants in high humidity conditions during at least one week to avoid its withering.

Preculture Medium (PCM)
MS basal salt mixture with 0.8% agar
Sucrose (30 g/l)
Myo-inositol (100 mg/l)
SH vitamins (10 ml/l)
IAA (4 mg/l)
Kinetin (4 mg/l)
Coculture Medium (CCM)
MS basal salt mixture with 0.8% agar
Sucrose (30 g/l)
Myo-inositol (100 mg/l)
SH vitamins (10 ml/l)
IAA (4 mg/l)
Kinetin (4 mg/l)
Acetosyringone (39.2 g/l)
Washing Medium (WM)
MS basal salt mixture
Sucrose (20 g/l)
Myo-inositol (100 mg/l)
Claforan (500 mg/l)
Recovery Medium (RM)
MS basal salt mixture with 0.8% agar
Sucrose (30 g/l)
Myo-inositol (100 mg/l)
SH vitamins (10 ml/l)
IAA (4 mg/l)
Kinetin (4 mg/l)
Claforan (300 mg/l)
Selection Medium (MS)
MS basal salt mixture with 0.8% agar
Sucrose (30 g/l)
Myo-inositol (100 mg/l)
SH vitamins (10 ml/l)
IAA (4 mg/l)
Kinetin (4 mg/l)
Zeatin (1 mg/l)
Kanamycin (50 mg/l)
Claforan (300 mg/l)
Rooting Medium (RM)
MS basal salt mixture with 0.8% agar
Sucrose (30 g/l)
Myo-inositol (100 mg/l)
Thiamine HCl (1 mg/l)
IAA (0.1 mg/l)

Characterization of the Lines RNAi 35S::SlBRC1L1 and 35S::SlBRC2L2.

10 independent transgenic lines were generated of the tomato plant, Moneymaker variety carriers of the construction 35S::SlBRC1L1 RNAi and another 10 carriers of the construction 35S::SlBRC1L2 RNAi which were phenotypically analysed. The T1 individuals indicated that, whilst the 35S::SlBRC1L1 RNAi individuals had a strong apical dominance (they had no branches), under the same conditions, the 35S::SlBRC1L2 RNAi individuals had a clear excess of lateral branches in comparison with the wild branches (FIGS. 1 and 2). These results show that the gene SlBRC1L2 has a greater importance than SlBRC1L1 in the control of lateral branch growth in the tomato plant.

Example 3

Cloning of the Genomic, Promoter and Coding Sequences of the Genes StBRC1L1 and StBRC1L2

To clone the orthologues to BRC1 of the potato plant a search was performed of BRC1-type TCP genes in different databases: TIGR Solanaceae Genomics Resource BLAST page, TIGR Plant Transcript Assemblies Database and SOL Genomics Network. To carry out the comparison, the sequence of amino acids of the TCP box of the BRC1 gene of *Arabidopsis* was used. Two unigenes were found: TC168465 and TC129597 which were called StBRC1L1 and StBRC1L2, respectively. Furthermore, knowing the high homology existing between tomato and potato, and having cloned the SlBRC1L1 tomato gene, the same primers were tested with genomic potato DNA, for end 5' Le1 (SEQ ID NO: 17) and Le2 (SEQ ID NO: 18), the latter being a nested primer of the previous, and Le3 (SEQ ID NO: 25) for end 3'. Based on this sequence a specific primer was designed (racest1-5\ SEQ ID NO: 34) to localize end 5' of the gene using the PCR-RACE technique with cDNA of axillary buds and stolons from potato. Based on the sequence obtained, a primer was designed at end 5': StTCPI-ORF1 (SEQ ID NO: 35). To amplify the cDNA sequence, a cDNA was used synthesized from the same RNA as for end 5', but using primer B26 (SEQ ID NO: 36) which includes in its sequence a polyT tail after the sequence of primer B25 (SEQ ID NO: 37), which makes it possible to use it as primer of end 3'.

The gene StBRC1L1 was amplified from DNA using the primers genomic-StTCPI A (SEQ ID NO: 38) and genomic-StTCPI B (SEQ ID NO: 39).

StBRC1L2 was first partially amplified from the same cDNA used for the StBRC1L1 gene. Primer B25 was used for end 3', and, for end 5' primers StTCP2A (SEQ ID NO: 40) and StTCP2B (SEQ ID NO: 41) (nested from the previous) were used, which had been designed depending on the sequence of the EST TC129597. From the sequence obtained, end 5' was localized using PCR-RACE and the specific primers St2-Seq 1 (SEQ ID NO: 42) and the nested one thereof. St2-Seq 2 (SEQ ID NO: 43).

For the amplification of the complete cDNA, the primers StTCP2-5' (SEQ ID NO: 44) and B25 were used. The sequence of the cDNA showed a series of polymorphisms which we consider as two alleles giving rise to allele 1 and allele 2, as well as to their respective proteins. For the genomic sequence, primers StTCP2-5' and StTCP2-3' (SEQ ID NO: 45) were used.

All amplified PCR fragments corresponding both to parts and all the sequences of the genes were clones in the pGEMT-easy™ vector (Promega).

Example 4

Generation of Transgenic Potato Plants (*Solanum tuberosum*, Desiree Variety) with Loss of Function of the Genes StBRC1L1 and StBRC1L2 Silenced by the RNAi Technique.

The fragment chosen for the interference of StBRC1L1 is situated between the TCP box and the R box, zones highly conserved and characteristic of the TCP genes. Said fragment does not ring with anything else but this part of the chosen sequence which guarantees a specific silencing of the StBRC1L1 gene. The fragment has 185 base pairs, and the sequence is included in the SEQ ID NO: 13, and constitutes the ninth polynucleotide of the invention.

The fragment chosen for the interference of StBRC1L2 is also situated between the TCP box and the R box. Said fragment only hybridizes with the part of sequence chosen, which guarantees the specific silencing of the gene StBRC1L2. The fragment has 168 base pairs, is included in the SEQ ID NO: 14, and constitutes the tenth polynucleotide of the invention.
Strategy used for the generation of the RNAi constructions for the genes StBRC1L1 and StBRC1L2.

To obtain the hairpin structure characteristic of the RNAi, the fragment selected was cloned in the pHannibal plasmid (CSIRO), which carried resistance to ampicillin. Said cloning is directed, so that the fragment enters in direction 5'-3' cloning it with the targets BamH I and Cla I, and at 3'-5' at the other end of the intron PDK (742 pb), using the targets Xho I and Kpn I. Therefore, the fragments selected were amplified using primers containing the target sequences for the different restriction enzymes to be used at end 5'.
For StBRC1L1
Primer of end 5': (SEQ ID NO: 46)
Primer of end 3': (SEQ ID NO: 47) For StBRC1L2
Primer of end 5': (SEQ ID NO: 48)
Primer of end 3': (SEQ ID NO: 49)

Once the recombinant plasmid has been obtained with the hairpin structure of the RNAi, and checked by sequencing, the pHannibal transgene (3330 pb) was extracted cutting with Not I and it was cloned in the site for the same restriction enzyme of the binary plasmid pART27 (Gleave, 1992 *Plant Mol. Biol.* 1992 December; 20(6): 1203-7) (FIG. 7), which confers resistance to streptomycin and to spectinomycin in bacteria and to kanamycin in plants. The NotI site of pART27 is localized between the right and left edges of the plasmid, which guarantees its transfer to the plant cell on transforming it. The transgene is flanked by the 35S promoter of the cauliflower mosaic virus (CaMV35S) (1346 pb) for a constitutive expression and end 3' of the octopine synthase gene (OCS terminator) (766 pb) of *Agrobacterium* which acts as transcription terminator.

Once the constructions in *Escherichia coli* have been obtained, a preparation was made of the plasmids used to transform *Agrobacterium tumefaciens* AGLO. A single colony was selected from the colonies carrying our plasmid, which was used to transform tomato plants.
Transformation of Potato Plants.

Potato plants were transformed grown in in vitro conditions in Murashige and Skoog medium with vitamins (*Physiol. Plant.* 15:473-497, 1962) supplemented with 2% sucrose (MS2). The plants must be between 3 and 4 weeks starting from the time when the plant apex is ringed in fresh medium.

The leaves are removed from the plant and the part of the petiole is eliminated with a scalpel and one or two cuts are made in the central vein, without these reaching the edges of the leaf. Ten of these leaves are placed with the top part downwards, in a 9 cm-diameter dish containing 10 ml of MS2 medium.

The dish is inoculated with 80 µl of the *Agrobacterium* culture. Said culture is initiated at an optical density (OD) at 600 nm of 0.2 in YEB medium with the suitable antibiotics. When it reaches an $OD_{600}$ nm of 0.8 it is washed by centrifugation and it is resuspended in the same volume of YEB medium without antibiotics, which is that used for inoculation.

The dishes are incubated during 2 days in the dark, but in the same temperature and humidity conditions wherein they are going to later grow. They then pass through a callus induction medium (CIM) maintaining the position of the leaves with the reverse downwards. After 7-8 days they are passed to the branch induction medium (BIM). They remain in this medium until the appearance of calluses and their development on leaves. The medium is refreshed every 8-10 days.

When the branches have between 0.5 and 1 cm they are transferred to the rooting medium consisting of MS medium with 1.6% of glucose, without any hormone, but with kanamycin (50 mg/L) and claforan (250 mg/L) to avoid the growth of *Agrobacterium*.

After rooting and when the plants have grown, the apex is cut and transferred to a MS2 medium with kanamycin and claforan in the same conditions indicated above.

For growing the plants in the greenhouse, plants which have been in MS2 medium between 1 and 2 weeks are transferred to receptacles with a capacity of 50 ml of substrate. The roots are covered with the substrate and the complete plant is covered with plastic to maintain the humidity, characteristic condition of in vitro growth. After 3-4 days said cover is removed.

Callus Induction Medium (CIM) MS with 1.6% Glucose
NAA (5 mg/L)
BAP (0.1 mg/L)
Claforan (250 mg/L)
Kanamycin (50 mg/L)
Plant Agar Duchefa (5.5 g/L)
Branch Induction Medium (MIR)
MS with 1.6% glucose
Zeatinroboside (2 mg/l)
NAA (0.02 mg/l)
GA₃ (0.02 mg/l)
Claforan (250 mg/l)
Kanamycin (50 mg/l)
Plant Agar Duchefa (5.5 g/l)

Characterization of the Lines RNAi 35S::StBRC1L1 and 35S::StBRC2L2.

In the potato plant there are several types of axillary buds: aerial buds which give rise to the branches, and the underground buds which give rise to the stolons, underground stems which tuberize giving rise to the tubers. The axillary buds of the stolons which are included in tubers are the tuber eyes.

Figure 3:
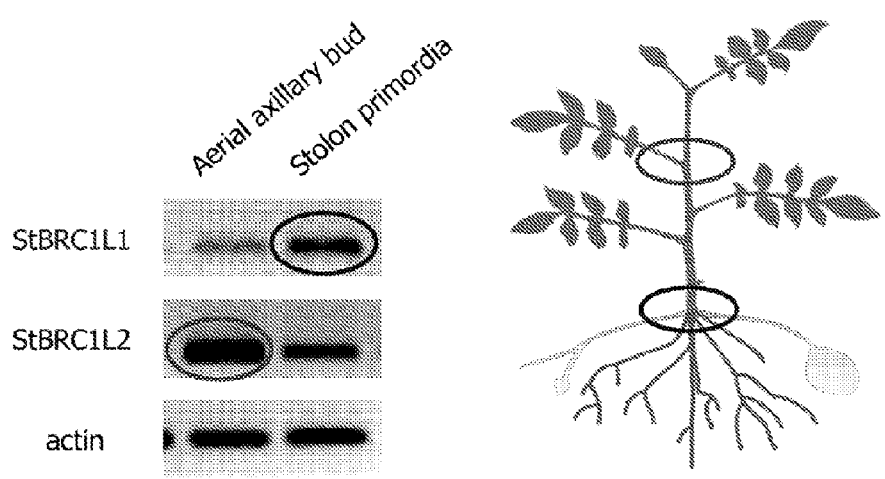
FIG. 3. Differential expression of the genes StBR1L1 and StBR1L2 in aerial buds and stolons, quantified by semiquantitative RT-PCR.

The results show that, in the potato plant, StBRC1L1 is expressed at higher levels in the stolon buds than in the aerial buds, whilst StBRC1L2 shows an inverse expression template (FIG. 3). This could reveal the specialization of each orthologue of BRC1 in the control of different types of buds.

The phenotype of the lack of function of StBRC1L1 supports its role in the suppression of the elongation and branching of the stolons. Seven transgenic lines of 35S::RNAiStBRC1L1 of potato, Desiree variety were generated, and they were analysed during two generations.

Figure 4:
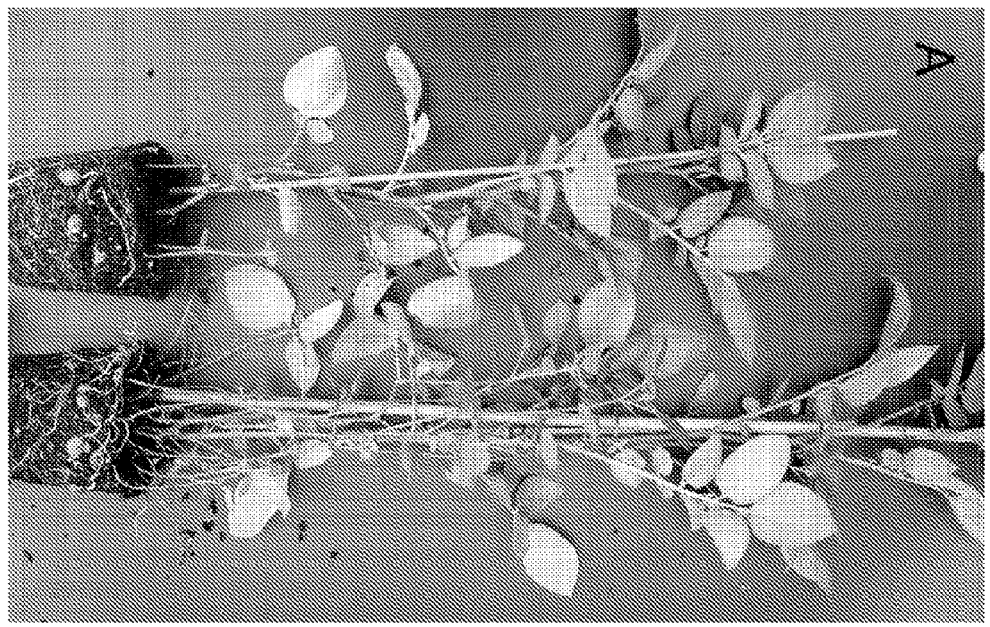
FIG. 4. Phenotype of transgenic potato lines with reduced activity of StBRC1L1. A. General aspect of Desiree variety control plant (left) and plant 35SCaMV:: StBRC1L1 RNAi (right). B. Phenotype of aerial branching of control plants and lines 35SCaMV:: StBRC1L1 RNAi. The x-axis represents the number of branches. C. Phenotype of underground branching (stolons) of control plants and lines 35SCaMV:: StBRC1L1 RNAi. The x-axis represents the number of stolons.
Figure 4:
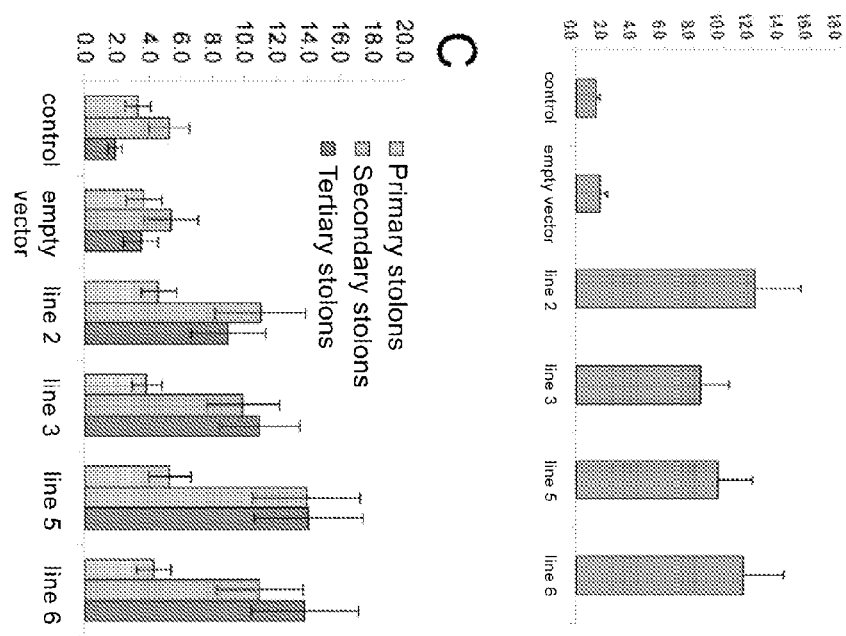
Figure 5:
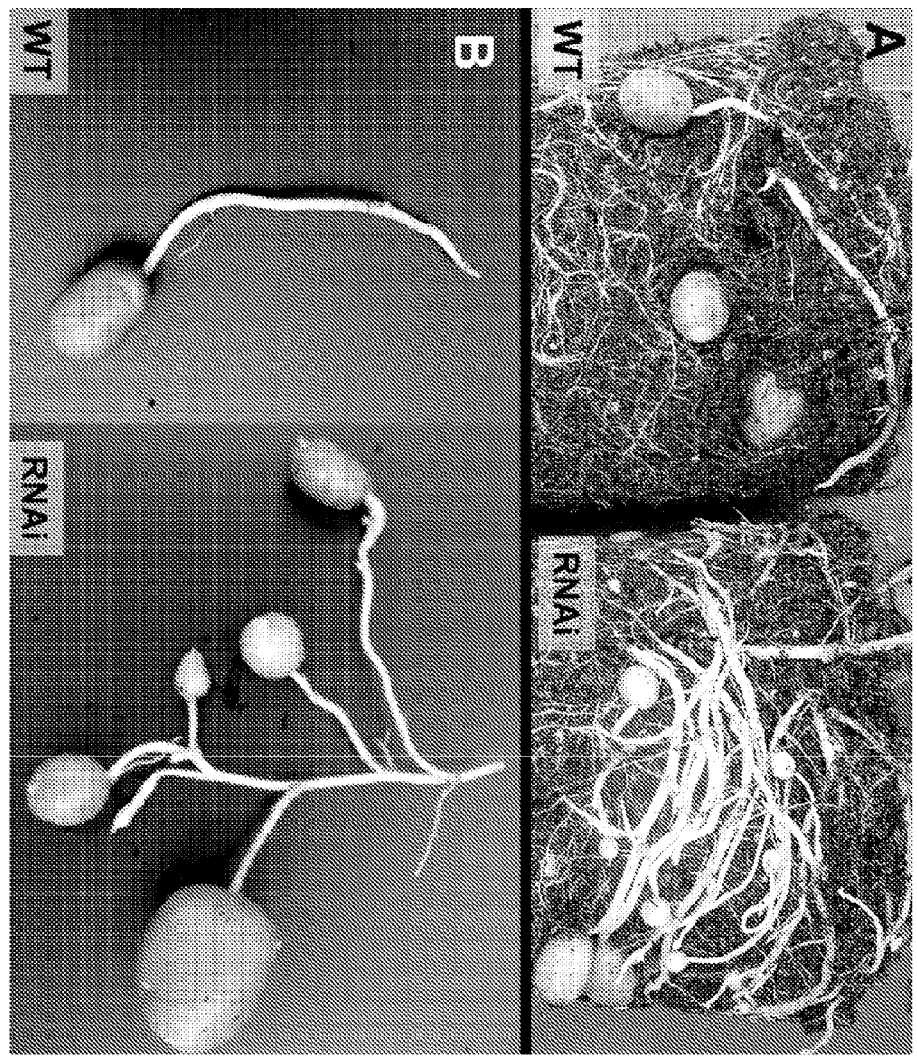
FIG. 5. Phenotype of stolons of lines 35SCaMV::RNAi StBRC1L1. A. The transgenic plants (RNAi) produce a greater number of stolons than the control plants (wt). B. Transgenic plants produce ramified stolons unlike the control plants.

StBRC1L1 affects both the development of the aerial branches and that of the stolons since the silenced lines have a greater number of lateral branches, aerial stolons and underground stolons (FIGS. 4 and 5).

Figure 6:
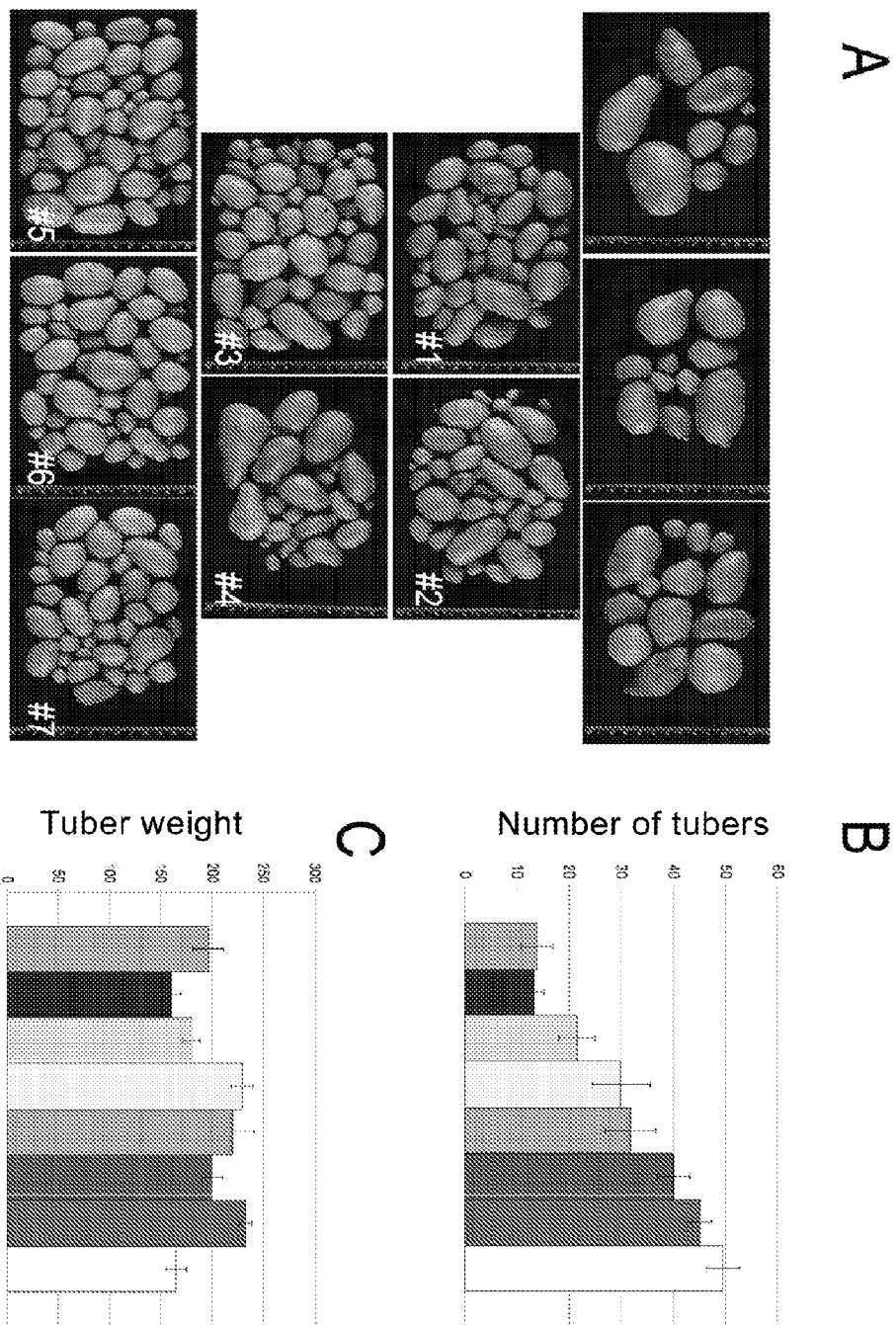
FIG. 6. Yield of the transgenic lines with reduced activity of StBRC1L1. A. Total production of tubers of control individuals (top) and individuals from independent lines 35SCaMV:: StBRC1L1 RNAi (bottom, numbered panels). B. Quantification of tuber production. C. Quantification of the total weight of tubers.

The underground stolons (which give rise to the tuber) are branched, unlike the wild stolons which show a strong apical dominance (FIG. 5). The tuberization time is not affected in these lines. Since each end of the stolon normally gives rise to a tuber, the high number of branched stolons makes each plant generate a greater number of tubers than wild plants (FIGS. 6A and 6B, 64-276.9% more than the controls). In the experimental conditions wherein the plants were grown (flowerpots of 20 cm diameter) a moderate increase was produced of the yield (17-19%) of the total weight of the tubers (FIG. 6C). It is very probable that in optimum conditions the yield is greater with respect to the wild plants. Furthermore, the lines are fairly vigorous and have delayed senescence.

The invention claimed is:

1. An isolated cDNA molecule capable of being translated into an amino acid sequence, said amino acid sequence comprising:
    a) a peptide having at least 95% identity with SEQ ID NO: 2, or
    b) the peptide having SEQ ID NO: 2;
    wherein said peptide maintains the function of suppressing the development of axillary buds and/or branch elongation in a plant.

2. An isolated cDNA molecule according to claim 1 operatively linked to a regulatory expression sequence of a gene of interest in the axillary meristem of a plant, wherein:
    a) the regulatory expression sequence comprises at least 95% identity with SEQ ID NO: 6, or
    b) the regulatory expression sequence is SEQ ID NO: 6.

3. A vector comprising:
    (a) an isolated cDNA molecule capable of being translated into an amino acid sequence said amino acid sequence comprising:
        (i) a peptide having at least 95% identity with SEQ ID NO: 2, or
        (ii) the peptide having SEQ ID NO: 2, wherein said peptide maintains the function of suppressing the development of axillary buds and branch elongation; or
    (b) a regulatory expression sequence operatively linked to the cDNA molecule according to (a), wherein:
        (i) the regulatory expression sequence comprises at least 95% identity with SEQ ID NO: 6, or
        (ii) the regulatory expression sequence is SEQ ID NO: 6.

4. A plant, a seed, a plant cell, a part of the plant or a grain of pollen comprising the vector according to claim 3 (a) or (b).

5. The plant, a seed, a plant cell, a part of the plant or a grain of pollen according to claim 4, which can be taxonomically classified as belonging to the species *Solanum lycopersicum*.

6. A method to reduce the number of branches of a plant with respect to a control plant, comprising:
    a) transfecting the isolated cDNA molecule according to claim 1, or a vector that comprises said cDNA molecule or a vector comprising a regulatory expression sequence operatively linked to said cDNA molecule, wherein the regulatory expression sequence comprises at least 95% identity with SEQ ID NO: 6, or the regulatory expression sequence is SEQ ID NO: 6, in a plant cell or culture of host plant cells, and (b) growing the transfected plant cell or culture of host plant cells in a suitable medium, until regenerating a complete plant.

7. The method according to claim 6, wherein the transfected cell can be taxonomically classified as belonging to the species *Solanum lycopersicum*.

8. A method for obtaining a plant having an increased number of branches with respect to a control plant comprising:
   (a) obtaining plant material from a plant (parent) which can be taxonomically classified as belonging to the species *Solanum lycopersicum;*
   (b) subjecting the plant material of step (a) to a mutagenesis process;
   (c) culturing the mutated plant material until regenerating a complete plant, and its descendants;
   (d) analysing the descendants of the plants of step (c) to detect at least one loss of function mutation in at least one copy of a polynucleotide encoding a peptide having at least 95% identity with SEQ ID NO: 2 or the peptide having SEQ ID NO: 2;
   (e) selecting the descendants of the mutated plant with said at least one mutation in at least one copy of said polynucleotide; and
   (f) optionally, culturing the plant selected to obtain further descendants with said at least one mutation.

* * * * *